US012345528B2

(12) United States Patent
Stromski et al.

(10) Patent No.: US 12,345,528 B2
(45) Date of Patent: Jul. 1, 2025

(54) OPTICAL COHERENCE TOMOGRAPHY WITH SELF-INSPECTING IMAGING DEVICE

(71) Applicant: LightLab Imaging, Inc., Westford, MA (US)

(72) Inventors: Steven M. Stromski, Windham, NH (US); Chih-Hao Liu, Chelmsford, MA (US)

(73) Assignee: LightLab Imaging, Inc., Westford, MA (US)

( * ) Notice: Subject to any disclaimer, the term of this patent is extended or adjusted under 35 U.S.C. 154(b) by 183 days.

(21) Appl. No.: 18/177,477

(22) Filed: Mar. 2, 2023

(65) Prior Publication Data

US 2023/0280153 A1     Sep. 7, 2023

Related U.S. Application Data

(60) Provisional application No. 63/316,071, filed on Mar. 3, 2022.

(51) Int. Cl.
*G01B 9/02091* (2022.01)
*G01B 9/02015* (2022.01)
*G01B 9/02055* (2022.01)

(52) U.S. Cl.
CPC ..... *G01B 9/02091* (2013.01); *G01B 9/02015* (2013.01); *G01B 9/02055* (2013.01)

(58) Field of Classification Search
CPC ............ G01B 9/02091; G01B 9/02015; G01B 9/02055
See application file for complete search history.

(56) References Cited

U.S. PATENT DOCUMENTS

2004/0173733 A1   9/2004   Korn
2011/0178413 A1*   7/2011   Schmitt ................ A61B 5/0084
                                                                    600/478

(Continued)

FOREIGN PATENT DOCUMENTS

CN         111917436 A   *   11/2020   ........... H04B 1/1027
WO        2014/153325 A1     9/2014
WO        2017139579 A1     8/2017

OTHER PUBLICATIONS

International Search Report and Written Opinion issued in Appln. No. PCT/US2023/014352 mailed Aug. 7, 2023 (26 pages).

*Primary Examiner* — Jamil Ahmed
(74) *Attorney, Agent, or Firm* — Lerner David LLP

(57) ABSTRACT

Aspects of the disclosure provide for automated self-inspection by an OCT imaging engine or device, to identify and resolve failures or inefficiencies in the hardware and/or software of the system or device during imaging. An OCT imaging engine can include a catheter connection check system for checking the quality of a physical connection point between a catheter and other components of an OCT imaging device or system. In some examples, the OCT imaging engine includes a self-inspection engine implemented to perform routine self-inspection by using a reference reflector internal to the OCT imaging engine to generate system performance data. The OCT imaging engine can use the system performance data to periodically search for and resolve failures or inefficiencies in the system. The OCT imaging engine can perform a self-calibration process to perform k-linearization and/or correct for chromatic dispersion using mirror measurements collected from an internal reference reflector.

22 Claims, 17 Drawing Sheets

(56) References Cited

U.S. PATENT DOCUMENTS

2013/0271768 A1   10/2013   Takaoka et al.
2020/0085285 A1   3/2020    Yamada

\* cited by examiner

OPTICAL COHERENCE TOMOGRAPHY WITH SELF-INSPECTING IMAGING DEVICE

CROSS-REFERENCE TO RELATED APPLICATION

The present application claims the benefit of the filing date of U.S. Provisional Patent Application No. 63/316,017 filed Mar. 3, 2022, the disclosure of which is hereby incorporated herein by reference.

BACKGROUND

Optical Coherence Tomography (OCT) is an imaging technique that uses light to capture cross-sectional images of tissue on the micron scale. OCT can be used both in situ or in systems external to a sample, such as an organism or tissue.

A common issue for OCT imaging devices is poor image quality of images generated by the devices. Example causes of poor image quality include hardware issues for either a probe or catheter used in imaging a subject, or hardware connections between the probe or catheter and other components of an OCT imaging device. Poor image quality may also be due to issues in software used to receive light signals from hardware sensors and to convert those signals into tomograms or other images. In some cases, the OCT imaging device may have multiple points of failure. Addressing those points of failure may require that the device be serviced by a trained field service technician, adding to downtime and cost.

BRIEF SUMMARY

Aspects of the disclosure provide for automated self-inspection by an OCT imaging engine or device, to identify and resolve failures or inefficiencies in the hardware and/or software of the system or device during imaging. An OCT imaging engine can include a catheter connection check system for checking the quality of a physical connection point between a catheter and other components of an OCT imaging device or system. In some examples, the OCT imaging engine includes a self-inspection engine implemented to perform routine self-inspection by using a reference reflector internal to the OCT imaging engine to generate system performance data. The OCT imaging engine can use the system performance data to periodically search for and resolve failures or inefficiencies in the system, without user input or the use of devices external to the system, such as external tools. The performance data collected by the system can also be monitored for trends to spot system degradation prior to failure. In some examples, the OCT imaging engine can perform a self-calibration process to perform k-linearization or correct for chromatic dispersion, which can automatically improve the performance of an OCT imaging engine through increased image quality. In yet another aspect, an OCT imaging engine may implement both the catheter connection check system and the self-inspection engine, as described herein.

Aspects of the disclosure provide for an imaging system including a light source adapted to be coupled to a first optical connector; a catheter adapted to be coupled to a second optical connector, the catheter adapted to be coupled to the light source using the first optical connector and the second optical connector; an interferometer including a plurality of optical switches, at least two of the plurality of optical switches connected together by a length of optical fiber, when in a first position, the plurality of optical switches create a first optical path for optical signals to pass to and from the light source and the catheter, and when in a second position, the plurality of optical switches create a second optical path for optical signals to pass to and from a light source along the length of optical fiber; and one or more processors configured to perform operations including: receiving a back reflection of an optical signal at a connection point between the first and second optical connectors; and determining, based on the back reflection, whether the catheter is fully connected or not fully connected to the light source.

Aspects of the disclosure provide for a method performed by one or more processors of an imaging system, the system including a light source adapted to be coupled to a first optical connector; a catheter adapted to be coupled to a second optical connector, the catheter adapted to be coupled to the light source using the first optical connector and the second optical connector; an interferometer including a plurality of optical switches, at least two of the plurality of optical switches connected together by a length of optical fiber, when in a first position, the plurality of optical switches create a first optical path for optical signals to pass to and from the light source and the catheter, and when in a second position, the plurality of optical switches create a second optical path for optical signals to pass to and from a light source along the length of optical fiber. The method includes receiving a back reflection of an optical signal at a connection point between the first and second optical connectors; and determining, based on the back reflection, whether the catheter is fully connected or not fully connected to the light source.

Aspects of the disclosure provide for one or more non-transitory computer-readable storage media storing instructions that when executed by one or more processors of an imaging system including a light source adapted to be coupled to a first optical connector; a catheter adapted to be coupled to a second optical connector, the catheter adapted to be coupled to the light source using the first optical connector and the second optical connector; an interferometer including a plurality of optical switches, at least two of the plurality of optical switches connected together by a length of optical fiber, when in a first position, the plurality of optical switches create a first optical path for optical signals to pass to and from the light source and the catheter, and when in a second position, the plurality of optical switches create a second optical path for optical signals to pass to and from a light source along the length of optical fiber, causes the one or more processors to perform operations including receiving a back reflection of an optical signal at a connection point between the first and second optical connectors; and determining, based on the back reflection, whether the catheter is fully connected or not fully connected to the light source.

Aspects of the disclosure provide for an imaging system including: a light source adapted to be coupled to a first optical connector; a catheter adapted to be coupled to a second optical connector, the catheter adapted to be coupled to the light source using the first optical connector and the second optical connector; an interferometer including one or more optical switches and a reference reflector coupled to a first optical switch of one or more optical switches; and one or more processors configured to perform operations including: receiving an optical signal reflected by the reference reflector; and calculating system performance data, including one or more of: a point spread function, a noise level, a signal-to-noise ratio, or a dynamic range.

Aspects of the disclosure provide for an imaging system including: a light source adapted to be coupled to a first optical connector; a catheter adapted to be coupled to a second optical connector, the first optical connector adapted to be coupled to the light source using the first optical connector and the second optical connector; an interferometer including one or more optical switches and a reference reflector coupled to a first optical switch of one or more optical switches; and one or more processors configured to perform operations including: receiving one or more mirror measurements using the reference reflector and the reference mirror; performing, using the one or more mirror measurements, one or more of: calculating a dispersion-free k-spectrum; calculating a polynomial fit for the dispersion-free k-spectrum; calculating a dispersion spectrum; or calculating a spectral-flattening spectrum; and saving one or more of the calculated spectra and the polynomial fit as calibration spectra to memory.

Aspects of the disclosure can include one or more features, including the features described below. In some examples, aspects of the disclosure provide for all of the features, in combination.

In determining, based on the back reflection, whether the catheter is fully or not fully connected to the light source, the one or more processors are further configured to perform operations including: calculating a return loss of the back reflection; and determining whether the catheter is fully connected or not fully connected to the light source based on a comparison between the calculated return loss and a predetermined return loss threshold.

The one or more processors are further configured to perform operations including: in response to the determination that the catheter is not fully connected, performing one or more of: outputting a prompt or signal indicating a potential issue with the catheter, and outputting data characterizing a quality of the physical connection between the catheter and the light source.

The one or more processors are further configured to perform operations including: in response to the determination that the catheter is fully connected, performing one or more of: outputting a prompt or signal indicating that the catheter is fully connected, and outputting data characterizing a quality of the physical connection between the catheter and the light source.

A sample arm includes a reference reflector coupled to a third optical switch of the plurality of optical switches, and wherein the one or more processors are further configured to perform operations including: receiving an optical signal reflected by the reference reflector; and calculating system performance data, including one or more of: point spread function, noise level, signal-to-noise ratio, or dynamic range.

The one or more processors are further configured to perform operations including: comparing the system performance data against one or more predetermined thresholds; and outputting a result corresponding to the comparison.

The one or more processors are further configured to perform operations including: comparing the system performance data against system performance data generated at an earlier point in time; and outputting a result corresponding to the comparison.

The one or more processors are configured to perform operations including: determining that the system has been powered on; and receiving the optical signal and calculating the system performance data in response to determining that the system has powered on.

The sample arm includes a reference reflector coupled to a third optical switch of the plurality of optical switches, and wherein the one or more processors are further configured to perform operations including: receiving one or more mirror measurements using the reference reflector and the reference mirror; performing, using the one or more mirror measurements, one or more of: calculating a dispersion-free k-spectrum; calculating a polynomial fit for the dispersion-free k-spectrum; calculating a dispersion spectrum; or calculating a spectral-flattening spectrum; and saving one or more of the calculated spectra and the polynomial fit as calibration spectra to memory.

The one or more mirror measurements include a plurality of mirror measurements taken from the reference reflector positioned on either side of a zero-delay line.

The one or more processors are further configured to perform operations including: loading the calibration spectra; and performing, using the loaded calibration spectra, one or more of: k-linearization, dispersion correction, or spectral flattening.

The one or more processors are further configured to perform operations including: receiving the back reflection of the optical signal at the connection point while the catheter is not connected to the light source; and determining, based on a return loss for the back reflection of the optical signal at the connection point while the catheter is not connected to the light source, whether the connection point is degraded.

The one or more processors are further configured to perform operations including: receiving one or more mirror measurements using the reference reflector and the reference mirror; performing, using the one or more mirror measurements, one or more of: calculating a dispersion-free k-spectrum; calculating a polynomial fit for the dispersion-free k-spectrum; calculating a dispersion spectrum; or calculating a spectral-flattening spectrum; and saving one or more of the calculated spectra and the polynomial fit as calibration spectra to memory.

The one or more processors are further configured to perform operations including: loading the calibration spectra; and performing, using the loaded calibration spectra, one or more of: k-linearization, dispersion correction, or spectral flattening.

A sample arm includes a plurality of optical switches, at least two of the plurality of optical switches connected together by a length of optical fiber, when in a first position, the plurality of optical switches create a first optical path for optical signals to pass to and from the light source and the catheter, and when in a second position, the plurality of optical switches create a second optical path for optical signals to pass to and from a light source and the length of optical fiber; and one or more processors configured to perform operations including: receiving a back reflection of an optical signal at a connection point between the first and second optical connectors; and determining, based on the back reflection, whether the catheter is fully connected or not fully connected to the light source.

DETAILED DESCRIPTION

Overview

Figure 1A:
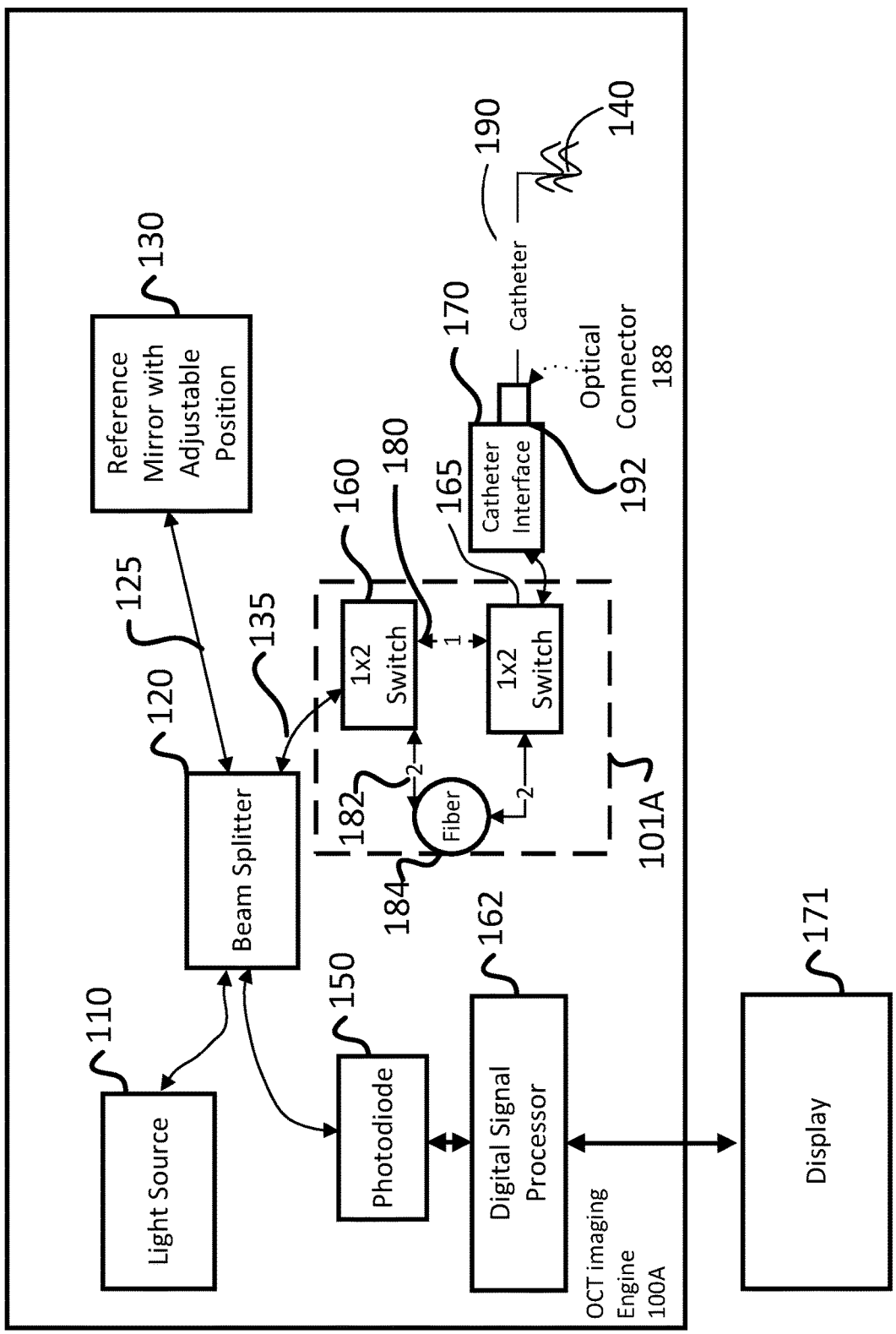
FIG. 1A is a block diagram of an example OCT imaging engine having a catheter connection check system, according to aspects of the disclosure.

Aspects of the disclosure provide for an OCT imaging engine configured to perform automatic self-inspection to identify and address inefficiencies or points of failure affecting the quality of images generated by the system. In some aspects of the disclosure, an OCT imaging engine can automatically check the quality of optical connectors forming a physical connection between a catheter and another component of the OCT imaging engine, such as a catheter interface configured to connect the catheter to the OCT imaging engine. The OCT imaging engine can use an internal length of optical fiber and an optical switch to measure a return loss of optical signal reflected at a physical connection point for the optical connectors. The internal length of fiber can be equal to or substantially similar to the length of an attached catheter, for example plus or minus two centimeters. In other examples, the internal length of fiber can vary in accordance with a maximum distance at which the reference mirror 130 can be adjusted, as described herein.

Based on the return loss, the OCT imaging engine can determine whether the connection is optimal or not, for example by comparing the return loss to a predetermined threshold. An "optimal" connection as used in this specification can refer to a connection with little—within a predetermined tolerance—or no degradation occurring in the passage of optical signals across the connection. Sources of degradation can include an improper coupling between optical connectors (for example, leading to an air gap between optical connectors), debris at the connection point of the optical connectors, such as dirt or dust, or an air gap between the optical connectors preventing glass-to-glass contact.

The connection point between two optical connectors may be a point of failure if optical signals are unable to be transmitted across the connection point. The connection point between two optical connectors may be considered degraded if optical signals can be transmitted across the connection point, but at a reduced rate or inferior quality relative to a connection point without any sources of degradation. Optical signal transmitted at an inferior quality can refer to signal loss or drop during transmission across the connection point during an imaging procedure.

If the connection point is found to not be optimal, the OCT imaging engine can take any of a variety of different actions, including generating user output indicating a potential source of failure in the system. The OCT imaging engine, for example, may prompt a user to manually inspect the physical connection point, or to take actions to address the issue, for example by reseating the optical connectors, prompting a user to replace the optical connectors, or prompting the user to clean the optical connectors.

In some aspects of the disclosure, an OCT imaging engine includes an internal reference reflector, or calibration mirror, for automatically receiving information corresponding to the quality of the OCT imaging engine. The reference reflector may be inserted in the sample arm of the OCT imaging engine and can be used to receive optical signals for performing various diagnostic processes for quantifying the performance of the OCT imaging engine. For example, the OCT imaging engine can self-assess its performance by computing system performance data, which can include one or more of a point-spread function (PSF), a Full-Width Half Maximum (FWHM), a noise level, signal-to-noise ratio, and the dynamic range of the system. The reference reflector may be coupled to the rest of the OCT imaging engine through an optical switch, allowing the OCT imaging engine to switch between an imaging mode and a self-inspection mode.

The OCT imaging engine can provide the system performance data, for example after performing self-inspection. Self-inspection can be performed, for example, at start-up of the OCT imaging engine, or before an imaging procedure is to be performed by the system. The OCT imaging engine can determine whether the system performance data indicates system degradation, and output suggestions or prompts for addressing potential causes of the reduced system performance. Degraded performance could also prompt the system to re-calibrate itself.

The OCT imaging engine can also use the reference reflector and a reference mirror of its reference arm to perform self-calibration. The self-calibration can include one or more of the following: k-linearization, dispersion correction, and spectral flattening. Aspects of the disclosure provide for applying k-linearization, dispersion correction, and spectral flattening using a one-time calibration process and optical signals collected from the reference reflector and the reference mirror adjusted to various different positions. The self-calibration as described herein can provide for improved OCT imaging engine performance, for example increased image quality, without the need for a k-clock. Through self-calibration, the OCT imaging engine can correct for problems caused by hardware degradation, such as dispersion introduced by environmental conditions or degrading optical components of the system.

In some examples, the OCT imaging engine with self-inspection as described herein can be coupled to a cloud computing platform or other system for uploading system performance data and/or calibration data collected as part of self-inspection. The collected system performance data can be used to monitor the performance of different deployed OCT imaging engines. Through the collected system performance data, one or more processors may implement a predictive model, such as a machine learning model, for predicting when maintenance to an OCT imaging engine will be required, before the system goes down. Additionally, the collected system performance data can also be beneficial in designing new versions of the OCT imaging engines, to potentially mitigate or avoid issues resulting in poor image quality identified through the collected data.

In some aspects of the disclosure, an OCT imaging engine can implement one or more of catheter connection checking, self-inspection, and self-calibration. The OCT imaging engine can receive input causing the switching of one or more optical switches from an imaging mode to one of a number of different self-inspection modes. The OCT imaging engine can perform one or more the self-inspection processes described herein automatically and without user input. The processes can be performed quickly, for example in less than a second, allowing the system to perform self-inspection at various times during usage. The self-inspection coupled with automated troubleshooting can improve performance with less down time resulting in higher user satisfaction and cost savings through reducing the need for onsite field service.

Aspects of the disclosure provide for a number of technical advantages. An OCT imaging engine configured for self-inspection as described herein reduces or eliminates user input to identify and resolve points of failure or inefficiencies in the OCT imaging engine, which may occur for example, periodically as a result of continued use and wear of the device, or occasionally manifest as a result of the design of the OCT imaging engine. Because user input in resolving these points of failure can be reduced, aspects of the disclosure provide for automated troubleshooting, improving performance of the OCT imaging engine while reducing downtime otherwise caused by unaddressed issues. The OCT imaging engine can sample optical signals for generating calibration spectra, using a reference reflector internal to the system. Because the reference reflector is internal, the OCT imaging engine can perform the self-inspection and calibration automatically, without requiring an external device be connected to the system first.

Example Systems
Catheter Connection Checking

FIG. 1A is a block diagram of an example OCT imaging engine 100A having a catheter connection check system 101A. In some examples, OCT imaging engine 100A is or incorporates an optical interferometer. A person of skill in the art will appreciate that although one configuration of an OCT imaging engine is illustrated in FIG. 1A, variations of the system, and different implementations, such as in-vivo OCT imaging engines, are within the scope of the disclosure. In some examples, the OCT imaging engine 100A may include more, fewer, or different components than the components illustrated in the figures. The direction of optical signals, including light signals, or electrical signals, is indicated by arrows within FIG. 1A. Although the imaging engine 100A is described as using OCT, other imaging modalities may be used, for example intravascular ultrasound (IVUS), near infrared spectroscopy (NIRS), microOCT, or any other modality.

Light source 110 can be a swept laser source or a source of low-coherence light able to capture micrometer or lower levels of resolutions. In some examples, ultra-broad output of the wavelength of light is desirable. In some examples, a laser can be used as a light source. In yet other examples, a light-emitting diode can be used as a light source. In some examples, light generated at light source 110 can be sent through a collimation lens (not shown).

Light from light source 110 can be sent to beam splitter 120. Beam splitter 120 can be an optical device that splits a beam of light from light source 110 into two or more beams. Light split by beam splitter 120 can move to reference mirror 130 and to sample 140. Aspects of reference mirror 130 are explained further with respect to FIG. 2B. Sample 140 can be an organic tissue or other sample upon which OCT can be performed. In some examples, sample 140 can be studied internally as is the case with in-vivo OCT scans. An optical signal, for example light from the light source 110, can be reflected from both reference mirror 130 and sample 140 through an optical path which crosses the beam splitter 120 and directs the light to photodiode 150. Photodiode 150 can be a semiconductor or other device which converts light into an electrical current and enables the detection of light.

Current or another electrical signal is generated in photodiode 150 when photons or waves of light are incident to the photodiode. Photodiode 150 may contain one or more optical filters, lenses, or other components to focus light and increase a signal-to-noise ratio. Signals generated at photodiode 150 may be converted from an analog to a digital signal and processed by a digital signal processor 162. A digital signal processor can be a specialized microprocessor or integrated chip with architecture and/or software optimized for the operational needs of digital signal processing. In some examples, digital signal processor 162 can enable the information generated at photodiode 150 to be processed and sampled by a k-clock signal and converted into an image for display on display 171. As explained further below, the digital signal processor 162 can perform one or more of the steps described below with optimizing the image generated from studying or observing sample 140.

The digital signal processor can include or be one of one or more processors. Aspects of disclosure include processes and computer-readable instructions that cause one or more processors to perform the processes described herein. The one or more processors can include any of a variety of types of processors, including one or more central processing units (CPUs), graphic processing units (GPUs), field-programmable gate arrays (FPGAs), and/or application-specific integrated circuits (ASICs).

Display 171 can display an image related to sample 140. As non-limiting examples, display 171 may be a monitor, OLED screen, LCD screen, television, electroluminescent display, or quantum dot display. Other specialized screens or displays for specialized contrast ratios or ease of displaying OCT information can also be used as display 171.

The OCT system may also include a k-clock (not shown). When the arrival time of the signal from the k-clock output to the DSP 162 is not synced with the signal from the main interferometer to the DSP 162, the interferogram cannot be sampled correctly. As used in this disclosure, an interferogram or an interference pattern can be a pattern formed by wave interference, such as for example, by interference of waves of light from a reference arm 125 and a sample arm 135 of the OCT imaging engine 100A.

Syncing problems can be introduced by mismatched optical fiber lengths and electronic connections after a photodiode, such as the photodiode 150, which can be, for example, bandpass filters or electrical cable lengths. In some examples, only a few percent, such as 2-3% of the light can be transmitted to the k-clock. A k-clock for the OCT imaging engine can include a 90° phase shifter, zero-crossing detection units, XOR gate or an OR gate, or any combination of similar elements.

A separate beam splitter (not shown) can also split light to a k-clock and beam splitter 120. In some examples, a small amount of light can be transmitted through the beam splitter to the k-clock. The k-clock can also be coupled to a separate photodiode (not shown), which can be similar to photodiode 150 and be connected to the k-clock and analyze light incident on photodiode 191. The k-clock photodiode can be connected to digital signal processor 162. As a portion of the light is transmitted through the k-clock, that light can be analyzed separately from the light incident or obtained from the sample 140.

In some examples, fiber optics and related optical components, such as optical couplers, can be used in lieu or in conjunction with the components described herein. For example, a person of skill in the art will appreciate that rather than using a collimation lens and beam splitter, optical couplers can be used to achieve the same or an equivalent setup as described with respect to FIGS. 1A-2D. Light can take a pathway as determined by the fiber optic wire or other optical signal-carrying material. The use of optical fibers and optical couplers can provide a more robust and simpler optical setup for use in commercial OCT applications. In some examples, various components can be linked, controlled, and communicated with through a suitable computing system, such as environment 600 further described below with reference to FIG. 6.

The OCT imaging engine includes a catheter connection check system 101A, which can be located in the sample arm 135 as shown in FIG. 1A. The engine 101A can include two 1×2 optical switches, a first optical switch 160 and a second optical switch 165. In a first position, the optical switches 160, 165 cause optical signals to travel back and forth between a catheter interface 170 and the beam splitter 120, indicated by optical path 180.

An optical switch is a device for switching optical signals of one or more sources to one or more different destinations. The sources and destinations can be fiber-optic or other light-carrying cables for receiving or sending optical signals to and from devices connected to the optical switch through the cables. The optical switch can receive an input to switch the path of the optical signal from one or more sources to one or more destinations. An optical switch can be at least partially described according to the number of sources and destinations supported by the switch. For example, a 1×2 switch refers to a switch with one source receiving input from a single source, to one or both of two destinations. The optical switch can receive input specifying which of the two destinations receives the optical signal from the source. Other configurations are possible, such as 1×3 switches. The current configuration of the optical switch, for example passing optical signals from a first source to a second destination in the case of a 1×2, is referred to as its position.

When the switches 160, 165 are moved into a second position, the optical switches 160, 165 cause optical signals to pass through fiber 184, indicated by optical path 182. The fiber 184 is a length of fiber-optic or other optical signal-carrying cable. The length of the fiber 184 can be substantially equal to the length of catheter 190, for example plus or minus two centimeters. Differences in the length of the cable can be compensated by adjusting the position of the reference mirror 130. While the optical switches 160, 165 are in the second position, the OCT imaging engine 100A may be said to be operating in "catheter connection check" mode.

When the switches 160, 165 are in the first position, the length of the optical path from the optical signal reflected from the sample 140 matches the length of the reference arm 125. When the switches 160, 165 are in the second position, the length of the optical signal from the beginning of the catheter 190 at connection point 192 matches the length of the reference arm 125. Although the sample arm 135 is shown with two switches 160, 165, in some examples the sample arm 135 can be configured to receive and send optical signals through either the first or second optical paths, using more or fewer switches. For example, FIG. 5B shows an OCT imaging engine 100D with multiple fiber lengths for handling different lengths of catheters.

When the switches 160, 165 are switched to the second position and the optical signals travel along the optical path 182, the OCT imaging engine 100A can inspect the catheter interface connection and determine whether the connection is successful by measuring the return loss in the glass-to-glass connection between the optical connector 188 for the catheter 190 and the optical connector 188 for the catheter interface 170. Devices configured for OCT imaging have been observed to be able to detect back reflections, measured according to a return loss (for example, in decibels). For example, if the optical connector 188 for the catheter interface 170 is an angle-polished connector (APC), then it has been observed that measured return loss of the back reflection of the optical signal can be approximately −65 dB. The catheter interface 170 can include other types of connectors, for example sacrificial joints and/or fiber-optic rotary joints, among others.

When the catheter 190 is successfully connected to the catheter interface 170 there is a glass-to-glass connection at the optical connector connection point 192 (shown as the point in which the catheter interface 170 is adjacent to the optical connector 188), that will reduce the reflection from the catheter interface connector by minimizing the Fresnel reflection. Any contaminants, air gaps, damage, alignment issues, or other potential points of failure or inefficiencies will cause the return loss of the back reflection of the optical signal at the connection point 192 to be higher relative to the return loss when the connection is successful.

In addition to checking the optical connector connection point 192, the DSP 162 can also receive a return loss for optical signals reflecting from other components of the catheter interface 170, such as a sacrificial joint or some other optical connector. In these examples, the DSP 162 can determine, from the received return loss, whether components of the catheter interface 170 for connecting a catheter are damaged, without requiring that a catheter be connected. In doing so, the DSP 162 can output more specific prompts for potential sources of degradation or failure, at least because the catheter 190 can be removed as a potential problem. The DSP can receive the back reflection of the optical signal at the connection point while the catheter is not connected to the light source. The DSP can determine, based on a return loss for the back reflection of the optical signal at the connection point while the catheter is not connected to the light source, whether the connection point is degraded.

The DSP 162 can calculate the return loss of the back reflection of the optical signal. The DSP 162 is configured to receive input indicating that the switches 160, 165 are in the second position. Based on the received input, the DSP 162 can receive incoming optical signals and determine the return loss of the back reflection of the optical signal. The DSP 162 can compare the measured return loss against a predetermined threshold indicating a successful connection at the optical connector connection point 192.

If the DSP 162 determines that the return loss of the back reflection of the optical signal is not within the predetermined threshold, the DSP 162 may perform a number of different actions in response. The DSP 162 can send a signal causing user output of the OCT imaging engine 100A to visually or audibly indicate that there is a potential issue at the connection point 192. For example, the DSP 162 can cause an LED or other light designated to indicate the status of the connection point 192 to blink or turn a certain color (e.g., red). In addition, or alternatively, the DSP 162 can cause a user display to print a message indicating the status of the connection point 192. In yet other examples, the DSP 162 causes speakers coupled to the OCT imaging engine 100A to play a warning tone or some other audible indication of the potential issue at the connection point 192. The DSP 162 can indicate a potential fault in the optical connectors connecting the catheter interface 170 to the catheter 190, instead of in the catheter interface 170 or the catheter 190. As optical connectors are generally easier and less costly to replace than the catheter 190 itself, the DSP 162 can facilitate more efficient troubleshooting and remedying of issues in the OCT imaging engine 100A, automatically.

If the DSP 162 determines that the return loss of the optical signal is within the predetermined threshold, then the DSP 162 may perform a number of different actions in response. For example, the DSP may play a confirmation tone, cause an LED to blink, or turn a certain color (e.g., green), and/or cause a confirmatory message to be displayed on a display. In some examples, the DSP 162 may cause the switches to return to position one, and not cause any user output at the OCT imaging engine 100A to occur if the DSP determines that the return loss is within the predetermined threshold of a successful connection. As described herein, FIG. 1B is a block diagram of an example process 105B for self-inspection of an optical signal connection point between a catheter interface and a catheter.

The predetermined threshold for a return loss may be empirically derived, for example based on measurements of back reflections of optical signals at connection points predetermined to be successful. In some examples, the return loss for an optical signal at a successful connection point can be between 20-30 dB, although the return loss may vary for different optical connectors, catheters, catheter interfaces, and/or other components of an OCT imaging engine.

In some examples, the OCT imaging engine 100A is configured to perform a calibration to compute the predetermined threshold indicating a successful connection. This may be performed, for example, when different optical signal-carrying components of the OCT imaging engine 100A are replaced, potentially resulting in a different return loss for the optical signal at a successful connection point. In other examples, the calibration may be performed in response to detecting a variability in component return loss, for example exceeding a predetermined threshold.

Figure 1B:
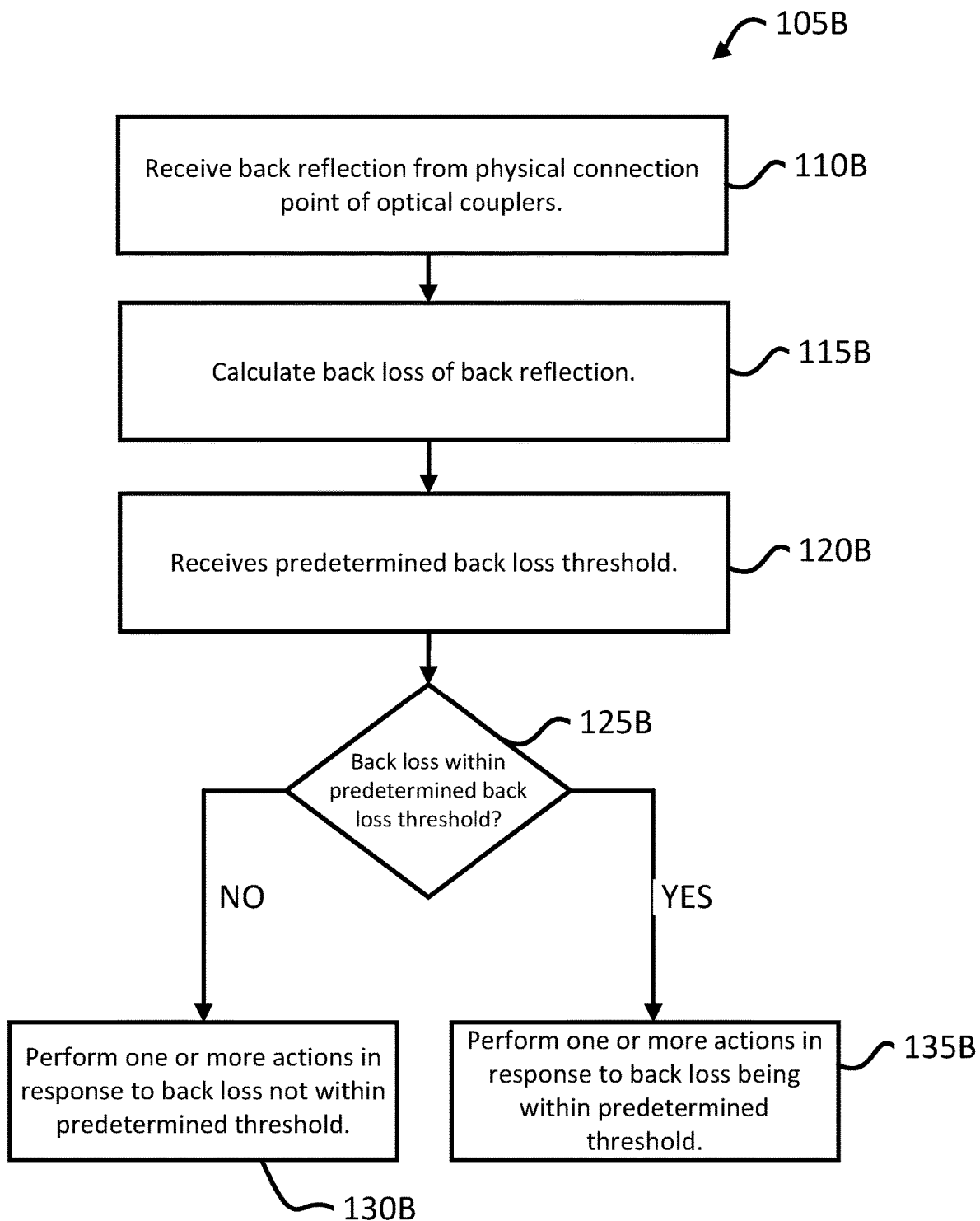
FIG. 1B is a flow diagram of an example process for performing a catheter connection check on an OCT imaging engine, according to aspects of the disclosure.

FIG. 1B is a flow diagram of an example process 105B for performing a catheter connection check on an OCT imaging engine.

The digital signal processor receives a back reflection from a physical connection point of optical connectors, according to block 110B. As described herein with reference to FIG. 1A, the back reflection can be received while the optical switches are set to a second position, or "catheter connection check" mode.

The digital signal processor calculates a return loss of the received back reflection, according to block 115B. In some examples, the OCT imaging engine can pass information characterizing the back reflection to another processor, for example external to the OCT imaging engine, for processing.

The digital signal processor receives a predetermined return loss threshold, according to block 120B. The DSP can receive the return loss threshold, for example from an external source, or calculate the return loss threshold as part of an initialization process whenever the OCT imaging engine is powered on or receives a replacement optical component.

The digital signal processor determines whether the calculated return loss is within the predetermined return loss threshold, according to decision block 125B. If so ("YES"), the DSP can perform one or more actions in response to the return loss being within the predetermined threshold, according to block 135B. The one or more actions can include outputting a prompt or signal indicating that the catheter is fully connected, and outputting data characterizing the quality of the physical connection between the catheter and the light source.

If the DSP determines that the calculated return loss is not within the predetermined return loss threshold ("NO"), then the DSP can perform one or more actions, according to block 130B, including outputting a prompt or signal indicating a potential issue with the catheter, and outputting data characterizing the quality of the physical connection between the catheter and the light source.

For example, by performing the process 105B, the OCT imaging engine can perform a self-inspection of its own performance during an optical imaging performance. In contrast to the use of external devices for measuring optical imaging equipment, or manual inspection for example by a field technician, the OCT imaging engine can automatically generate information used in assessing the performance of the system during operation. This process of automatically generating information related to system performance automatically and without external intervention can be referred to as "self-inspection." The calculated and compared return loss is an example of this type of information, at least because it is generated by the OCT imaging engine without external devices or manual inspection and provides insight into the quality of the optical connection between the catheter and the rest of the engine, which is used to determine the presence of degradation in the connection.

Figure 1C:
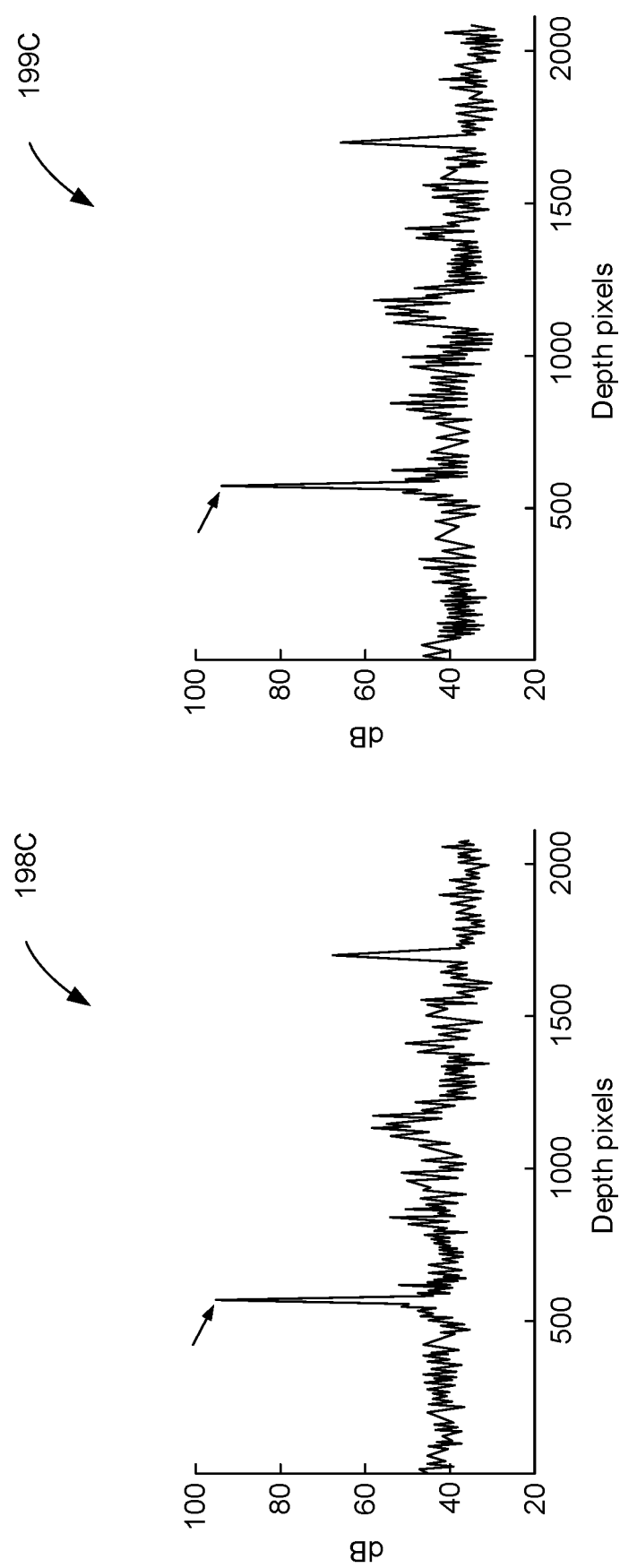
FIG. 1C shows example graphs illustrating return losses for a damaged catheter interface optical connector detected by the OCT imaging engine.

FIG. 1C shows example graphs 198C-199C illustrating return losses for a damaged catheter interface optical connector detected by the OCT imaging engine. The x-axis of the graphs 198C-199C track distance from the zero optical path difference in pixels, and the y-axis tracks return loss of the optical signal in decibels. Graph 198C shows the return loss at the optical connection point before the catheter is connected and has a peak return loss of approximately 90. Graph 199C shows the return loss of the back reflection at the optical connector connection point after the catheter is connected, with a similar peak return loss. Based on these measurements, the OCT imaging engine can determine a return loss threshold and use the threshold to compare return losses for damaged and undamaged optical components of the OCT imaging engine.

Figure 1D:
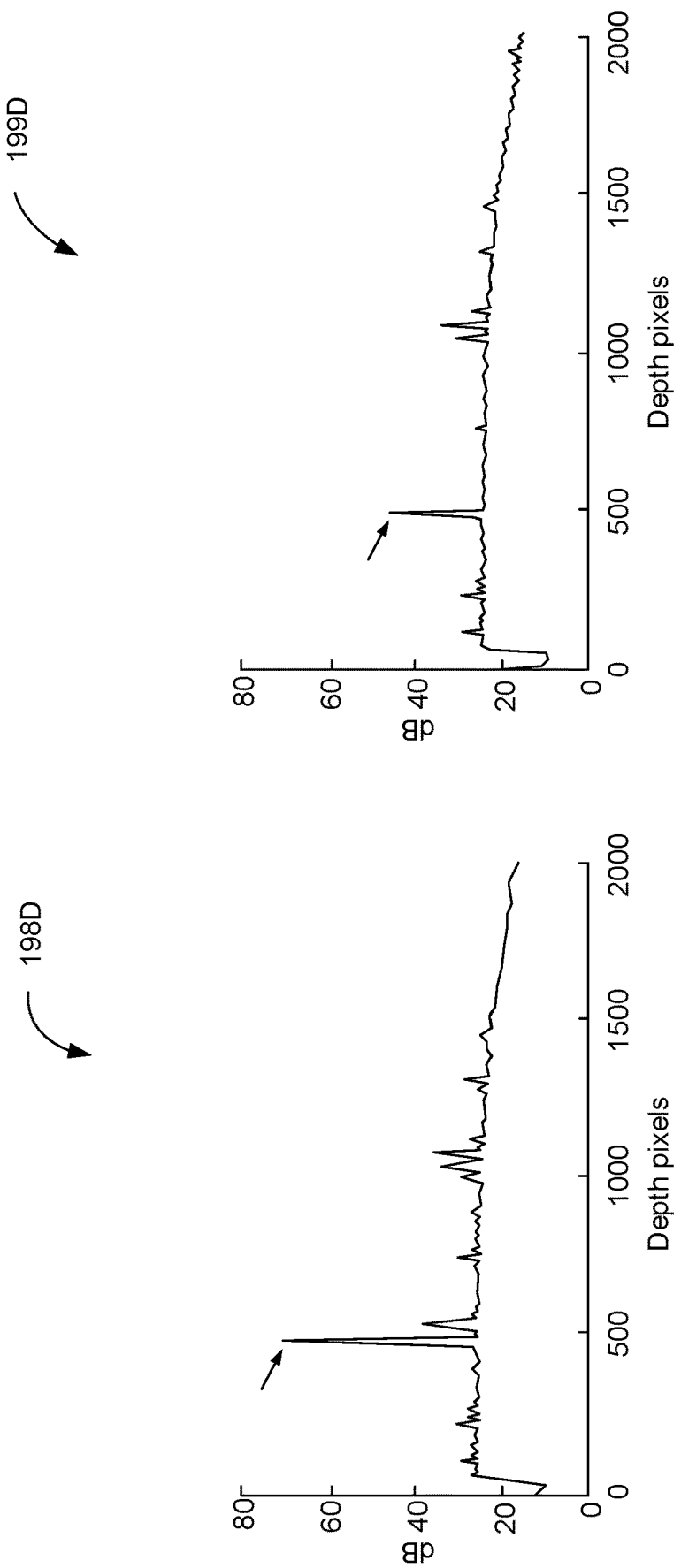
FIG. 1D shows example graphs illustrating return losses from the catheter interface before and after a successful catheter connection, as measured by the OCT imaging engine.

FIG. 1D shows example graphs 198D-199D illustrating return losses from the catheter interface before and after a successful catheter connection, as measured by the OCT imaging engine. The x-axis of the graphs 198D-199D tracks distance from the zero optical path difference in pixels, and the y-axis tracks return loss of the optical signal in decibels. Graph 198D shows the return loss of the optical connection point before the catheter is successfully connected, with a peak loss of about 70 dB. Graph 199D shows the return loss of the optical connection point after the catheter is connected, with a peak loss of about 50 dB, or about a 20-30 dB difference.

Figure 1E:
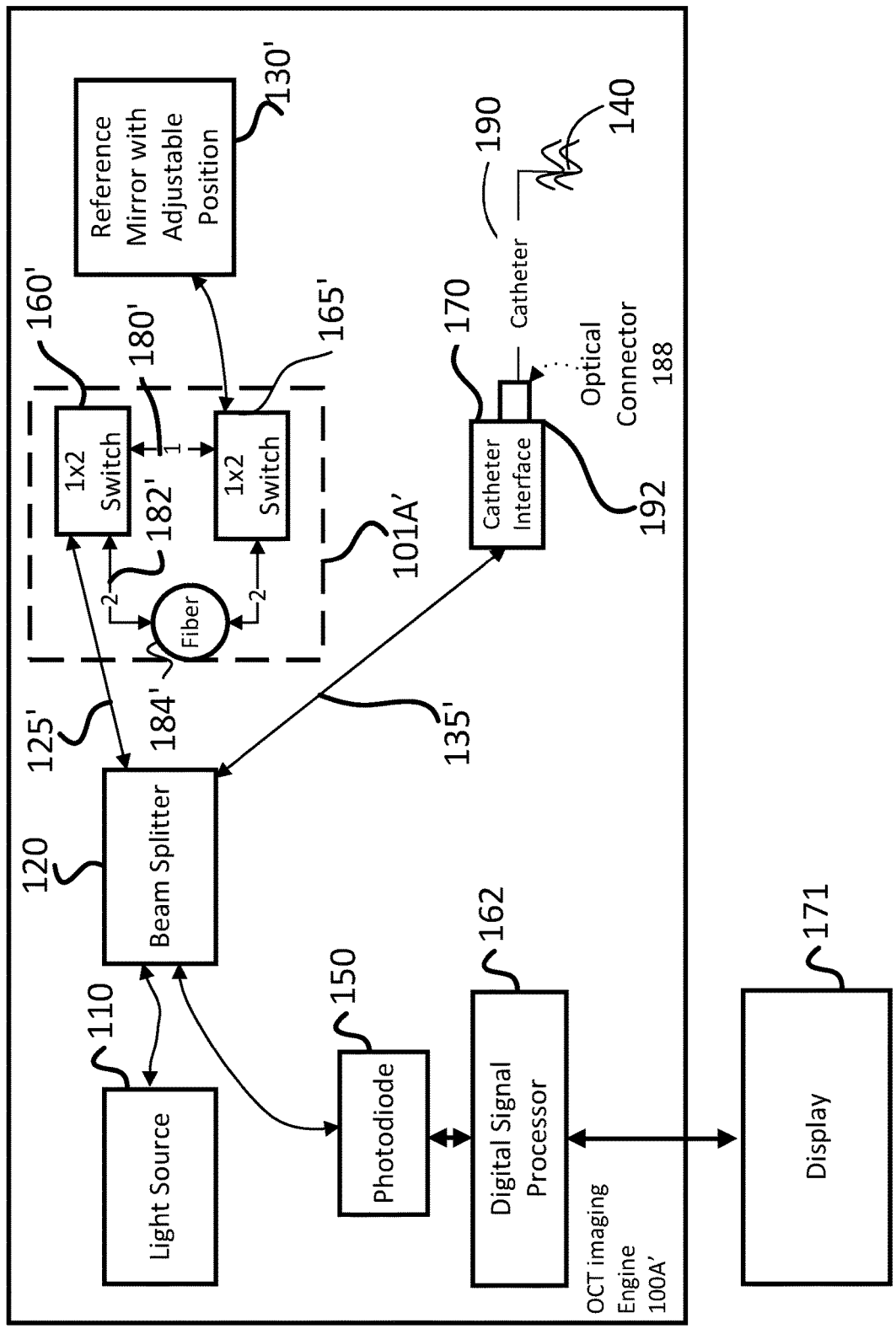
FIG. 1E is a block diagram of an example OCT imaging engine having a catheter connection check system, according to aspects of the disclosure.

FIG. 1E is a block diagram of an example OCT imaging engine 100A' having a catheter connection check system 101A'. OCT imaging engine 100A' can contain the same components and can be configured to operate in a similar manner as discussed herein in connection with OCT imaging engine 100A of FIG. 1A. However, as shown in FIG. 1E, components for catheter connection check system 101A' are contained within reference arm 125', rather than in sample arm 135'. The catheter connection check system 101A' can include two 1×2 optical switches, a first optical switch 160' and a second optical switch 165'. In a first position, the optical switches 160', 165' cause optical signals to travel back and forth between reference mirror 130' and the beam splitter 120, indicated by optical path 180'.

When the switches 160', 165' are changed into a second position, the optical switches 160', 165' cause optical signals to pass through fiber 184', indicated by optical path 182'. The fiber 184' is a length of fiber-optic or other optical signal-carrying cable. The length of fiber 184' may be configured based on the length of catheter 190, so that OCT imaging engine 100A' can check whether the catheter 190 has been properly connected to catheter interface 170. For example, the length of the fiber 184' can be substantially equal to the length of catheter 190, plus or minus two centimeters. Differences in the length of the cable can be compensated by adjusting the position of the reference mirror 130'. While the optical switches 160', 165' are in the second position, the OCT imaging engine 100A' may be said to be operating in "catheter connection check" mode.

When the switches 160', 165' are in the first position, the length of the optical path from the optical signal reflected from reference mirror 130' matches the length of sample arm 135' up to the connection point 192 for catheter interface 170. When the switches 160', 165' are in the second position, the length of the optical signal from the end of catheter 190 at sample 140 matches the length along reference arm 125' to reference mirror 130'. Although the reference arm 125' is shown with two switches 160', 165', in some examples the reference arm 125' can be configured to receive and send optical signals through either the first or second optical paths, using more or fewer switches.

When the switches 160', 165' are switched to the first position and the optical signals travel along the optical path 180', the OCT imaging engine 100A' can inspect the catheter interface connection and determine whether the connection is successful by measuring the return loss in the glass-to-glass connection at the connection point 192 between optical connector 188 and catheter interface 170. Devices configured for OCT imaging have been observed to be able to detect back reflections, measured according to a return loss (for example, in decibels). For example, if the optical connector 188 for the catheter interface 170 is an angle-polished connector (APC), then it has been observed that measured return loss of the back reflection of the optical signal can be approximately −65 dB. The catheter interface 170 can include other types of optical components, for example sacrificial joints and/or fiber-optic rotary joints, among others. The return loss of these components can also be measured.

When the catheter 190 is successfully connected to the catheter interface 170 there is a glass-to-glass connection at the optical connector connection point 192 (shown as the point in which the catheter interface 170 is adjacent to the optical connector 188), that will reduce the reflection from the catheter interface connector by minimizing the Fresnel reflection. Any contaminants, air gaps, damage, alignment issues, or other potential points of failure or inefficiencies will cause the return loss of the back reflection of the optical signal at the connection point 192 to be higher relative to the return loss when the connection is successful.

In addition to checking the optical connector connection point 192, the DSP 162 can also receive a return loss for optical signals reflecting from other components of the catheter interface 170, such as a sacrificial joint or some other optical connector. In these examples, the DSP 162 can determine, from the received return loss, whether components of the catheter interface 170 for connecting a catheter are damaged, without requiring that a catheter be connected. In doing so, the DSP 162 can output more specific prompts for potential sources of degradation or failure, at least because the catheter 190 can be removed as a potential problem. The DSP can receive the back reflection of the optical signal at the connection point while the catheter is not connected to the light source. The DSP can determine, based on a return loss for the back reflection of the optical signal at the connection point while the catheter is not connected to the light source, whether the connection point is degraded.

The DSP 162 can calculate the return loss of the back reflection of the optical signal. The DSP 162 is configured to receive input indicating that the switches 160', 165' are in the first position. Based on the received input, the DSP 162 can receive incoming optical signals and determine the return loss of the back reflection of the optical signal. The DSP 162 can compare the measured return loss against a predetermined threshold indicating a successful connection at the optical connector connection point 192.

If the DSP 162 determines that the return loss of the back reflection of the optical signal is not within the predetermined threshold, the DSP 162 may perform a number of different actions in response. The DSP 162 can send a signal causing user output of the OCT imaging engine 100A to visually or audibly indicate that there is a potential issue at the connection point 192. For example, the DSP 162 can cause an LED or other light designated to indicate the status of the connection point 192 to blink or turn a certain color (e.g., red). In addition, or alternatively, the DSP 162 can cause a user display to print a message indicating the status of the connection point 192. In yet other examples, the DSP 162 causes speakers coupled to the OCT imaging engine 100A' to play a warning tone or some other audible indication of the potential issue at the connection point 192. The DSP 162 can indicate a potential fault in the optical connectors connecting the catheter interface 170 to the catheter 190, instead of in the catheter interface 170 or the catheter 190. As optical connectors are generally easier and less costly to replace than the catheter 190 itself, the DSP 162 can facilitate more efficient troubleshooting and remedying of issues in the OCT imaging engine 100A', automatically.

Self-Assessment and Self-Calibration

Figure 2A:
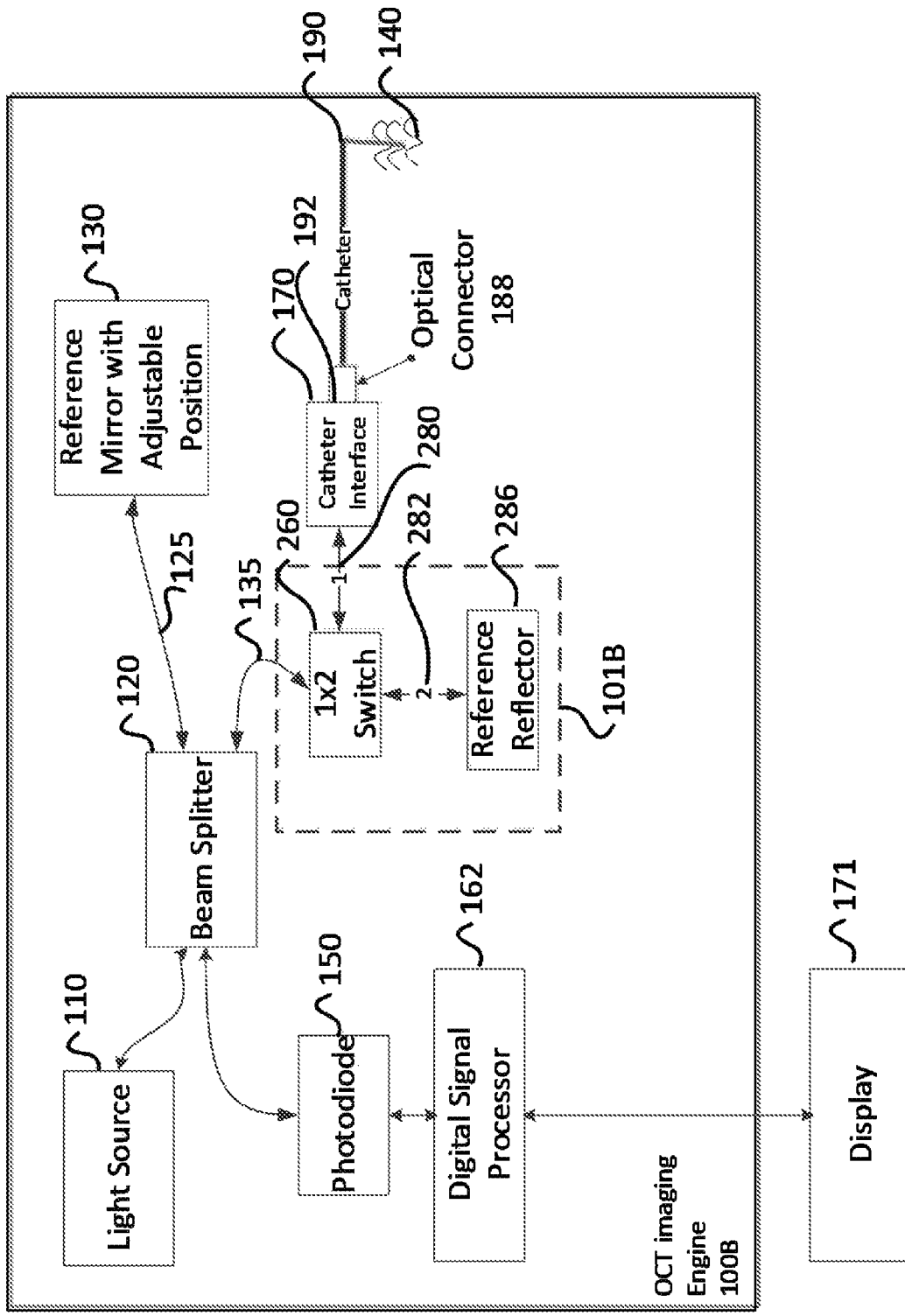
FIG. 2A is a block diagram of an example OCT imaging engine configured to perform self-assessment and calibration, according to aspects of the disclosure.

FIG. 2A is a block diagram of an example OCT imaging engine 100B configured to perform self-assessment and calibration.

OCT imaging engine 100B can include a self-assessment and calibration engine 101B, which can include an optical switch 260 and a reference reflector 286. The switch 260 can be 1×2, defining two optical paths 280, 282. In a first position, the switch 260 causes an optical signal to pass to and from the catheter interface 170, along optical path 280. In a second position, the switch 260 causes an optical signal to pass to and from the reference reflector 286 along optical path 282. While the switch 260 is in the second position, the OCT imaging engine 100 can be said to be in "self-assessment and calibration" mode.

The OCT imaging engine 100B can be further configured for simultaneously correcting for nonlinear sampling and chromatic dispersion, to automatically calibrate the system by optimizing the spectra using wavenumber linearization of k-linearization (KL), dispersion correction (DC), and spectral flattening. The system allows for calibration to be performed without an external k-clock to compensate for non-linear sampling in k-space.

The OCT imaging engine 100B can use one or more positions of the reference mirror 130 and the reference reflector to generate information related to the performance of the optical system and be used in the methods described herein. In some examples, information generated from positions P1 and P2 can be used to calculate the spectra wavelength linearization and the spectral flattening spectra, as further explained with reference to FIGS. 3-4B.

Figure 2B:
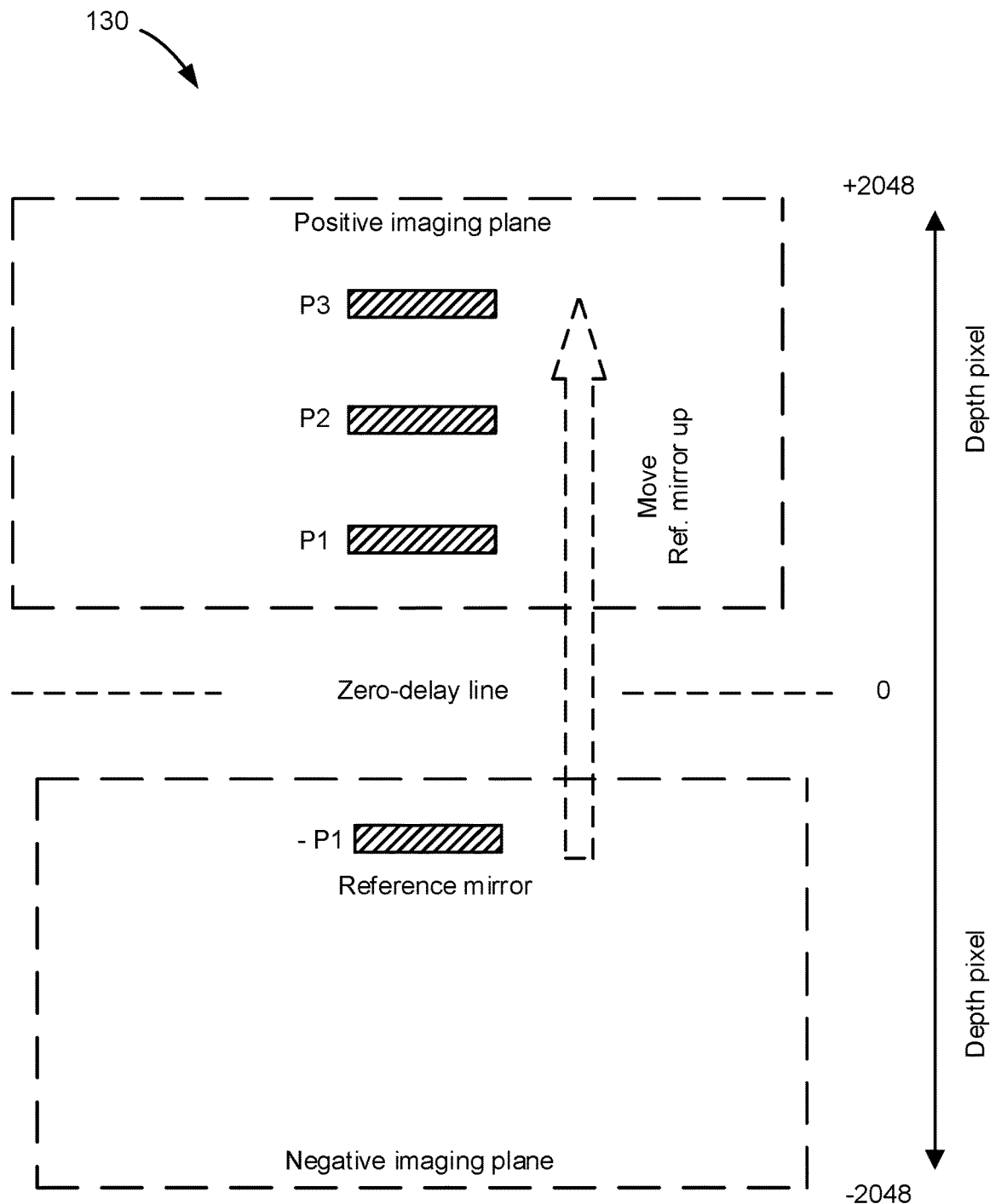
FIG. 2B is a schematic diagram of a reference mirror of the OCT engine, according to aspects of the disclosure.

FIG. 2B is a schematic diagram of reference mirror 130 of the OCT engine 100B, according to aspects of the disclosure. Reference mirror 130 can be a mirror or other reflective surface with high reflectivity and optical properties to enable reflection of photons. The OCT imaging engine 100B can scan the mirror 130 in the reference arm 125 along with an optical signal from Reference Reflector 286. The OCT imaging engine 100B using the DSP 162 can calculate an interference pattern and use the pattern to generate an interferogram or another type of image from the received signal.

The OCT imaging engine 100B is configured to adjust the position of the reference mirror 130. Referring to FIG. 2B, The OCT imaging engine 100B can adjust the reference mirror 130 to various positions on either side of a zero-delay line. Various positions, such as positions P1, P2, and P3 can move the image of the mirror to different depth pixels, for example ranging from −1024 to +1024 pixels relative to the zero-delay line. In some examples, the pixel depth for the various positions can depend on the total amount of pixel numbers used before a fast Fourier transform (FFT) is performed, according to k-clock total samples or internal sampling rate of A/D cards, and/or zero-padded data length before FFT. An example imaging depth from pixel depth 0 to pixel depth 1024 can be determined according to the following:

$$(\text{central wavelength})^2/(2*\text{laser bandwidth})$$

The pixel depth can depend on the half of the total amount of the pixel numbers used before FFT, according to k-clock total samples or internal sampling rate of A/D cards, and zero-padded data length before FFT.

The OCT imaging engine changes the interference pattern generated from light returning from Reference Reflector 286, by adjusting the position of the reference mirror 130. As described herein, the position of the reference mirror 130 can be used to generate information related to the performance of the OCT imaging engine 100B. For example, information generated from an interference pattern of light reflected by the reference mirror 130 while in one or more of the various positions described herein can be used by the OCT imaging engine 100B to calculate the spectra wavelength linearization and the spectral flattening spectra. In some examples, the position of reference mirror 130 can change the interference pattern generated from light returning from Reference Reflector 286.

Figure 2C:
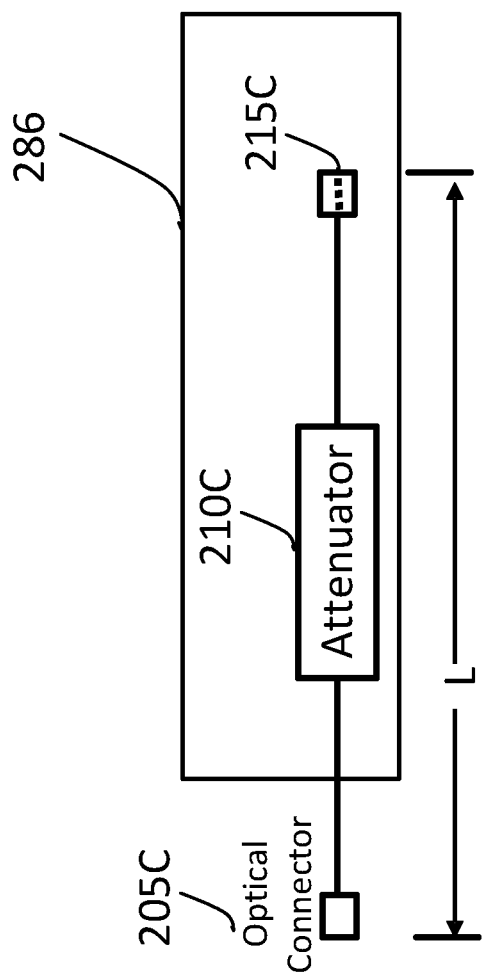
FIG. 2C is a block diagram of the reference reflector of FIG. 2A, according to aspects of the disclosure.

FIG. 2C is a block diagram of the reference reflector 286 of FIG. 2A, according to some examples. The reference reflector 286 can include an optical connector 205C, connecting the reference reflector 286 to the switch 260. Alternatively, the reference reflector 286 can be fusion spliced to connect to the switch 260. The reference reflector 286 can include an attenuator 210C. The attenuator 210C can have a predetermined attenuation, for example attenuating the reflected signal so the magnitude of the reflection is similar to a reflection from the sample 140, for example plus or minus 20 dB. The reference reflector 286 can include a flat surface 215C for providing a single-point reflection. The length of the optical fiber L can have a similar optical path length as the sample 140 so the light reflected from 215C will interfere with the reference arm, for example 1.6 meters. The single-point reflection may be referred to as the Point Spread Function (PSF) and may be processed by the DSP 160 or other component of the OCT imaging engine for obtaining information quantifying the OCT imaging engine.

According to some examples, the OCT imaging engine receives mirror measurements using the reference mirror and the calibration mirror. A mirror measurement can include a time-varying amplitude of an interferogram. The system can use the received measurements to retrieve the phase of the optical signal as a function of the sampling index.

Figure 2D:
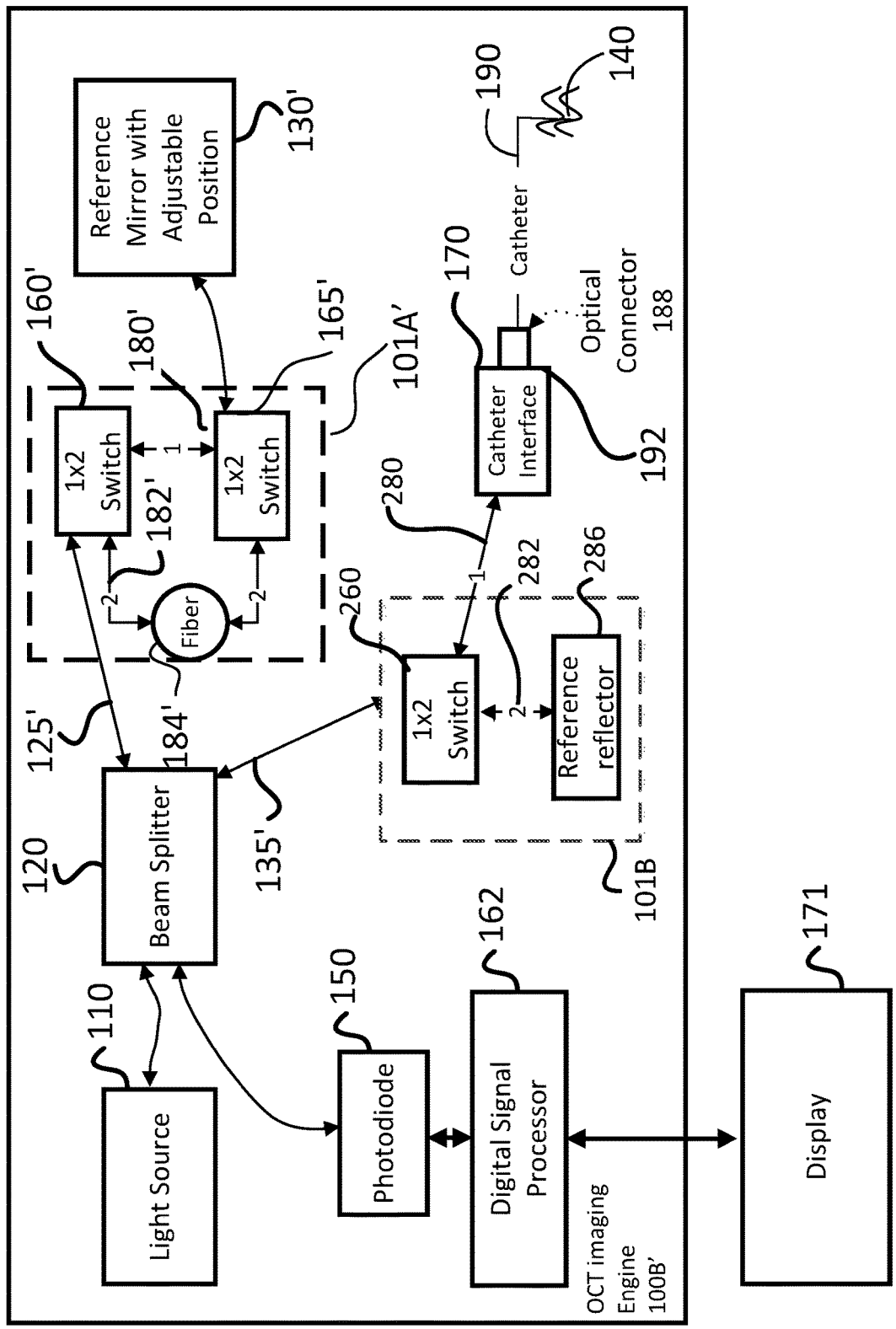
FIG. 2D is a block diagram of an example OCT imaging engine configured to perform self-assessment and calibration, according to aspects of the disclosure.

FIG. 2D is a block diagram of an example OCT imaging engine 100B' configured to perform self-assessment and calibration, and also configured with a catheter connection check system 101A'.

The OCT imaging engine 100B' can use one or more positions of the reference mirror 130' and the reference reflector to generate information related to the performance of the optical system and be used in the methods described herein. In some examples, information generated from positions P1 and P2 can be used to calculate the spectra wavelength linearization and the spectral flattening spectra, as further explained with reference to FIGS. 3-4B. In addition, OCT imaging engine 100B' can use catheter connection check system 101A' to check the connection of catheter 190 to catheter interface 170 in a manner described herein for the OCT imaging engine 100A' shown in FIG. 1E.

Figure 3:
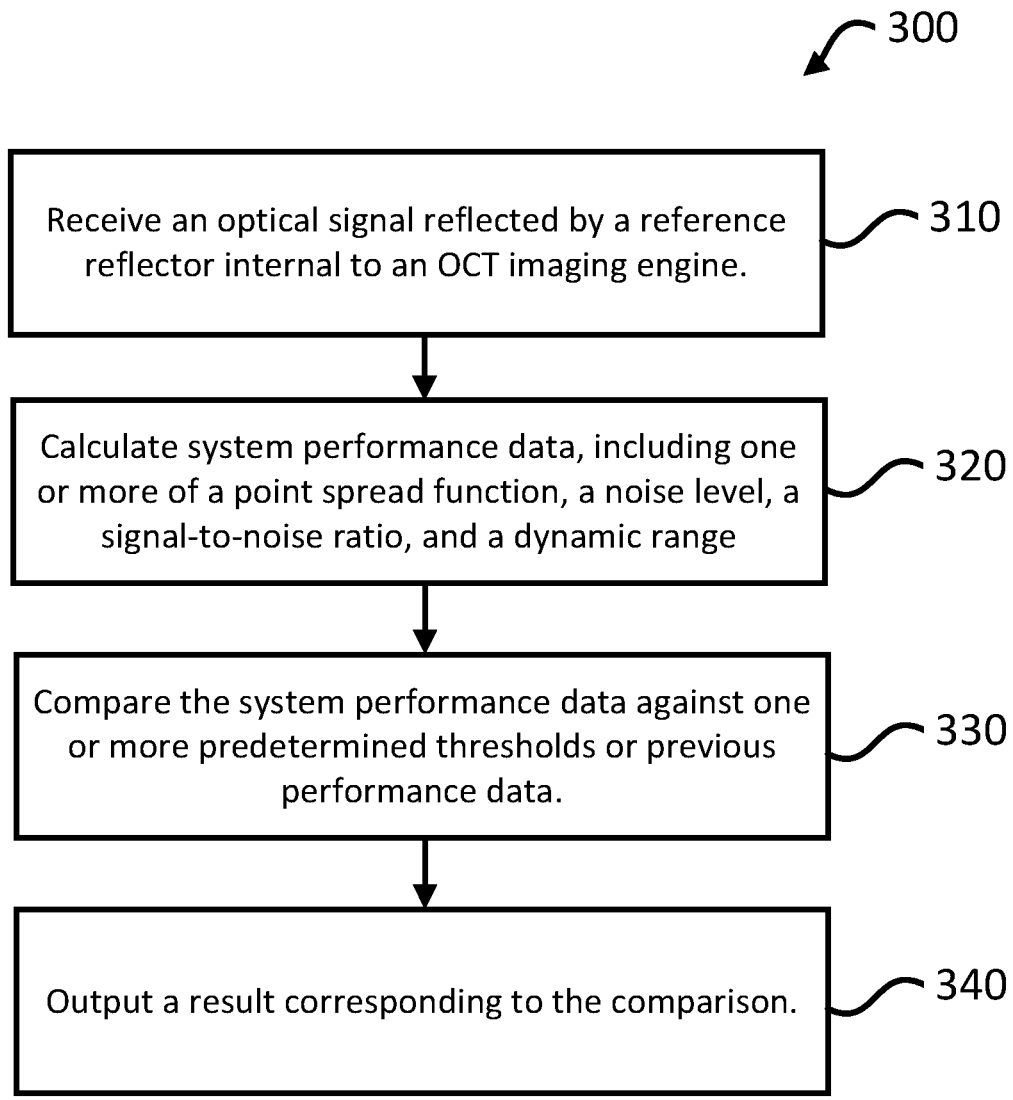
FIG. 3 is flow diagram of an example process for self-assessment by an OCT imaging engine, according to aspects of the disclosure.

FIG. 3 is a flow diagram of an example process 300 for self-assessment by an OCT imaging engine, according to aspects of the disclosure.

For example, the DSP 162 of FIG. 2A may receive input indicating that the switch 260 is set to the second position, for receiving the PSF from the reference reflector 286. The DSP 162 can use the PSF to measure, for example, the full-width half maximum (FWHM), a current or average noise level, a signal-to-noise ratio (SNR), and/or dynamic range of the OCT imaging engine.

The DSP 162 can compare this obtained data against known thresholds, which can be used by the DSP 162 to determine whether the OCT imaging engine is performing within acceptable parameters or not. For example, The DSP 162 can determine whether the SNF of the OCT imaging engine exceeds a predetermined SNF threshold. As a result of the determination, the DSP 162 can perform any of a variety of actions, for example those described above with reference to FIG. 1B, to send an indication that the OCT imaging engine may potentially not be operating correctly or efficiently.

According to FIG. 3, the DSP receives an optical signal reflected by a reference reflector internal to an OCT imaging engine, according to block 310.

The DSP calculates system performance data using the received optical signal, according to block 320. The system performance data can include one or more of a point spread function, a noise level, a signal-to-noise ratio, and a dynamic range.

The DSP compares the system performance data against one or more predetermined thresholds, or previous system performance data, according to block 330. The predetermined thresholds can correspond to the ideal system performance data an imaging engine should be producing under different settings. For example, for a certain calibration intensity, the DSP can compare the calculated system performance data with the predetermined thresholds, to determine whether the OCT imaging engine is performing within parameters. The DSP can also monitor trends in the performance data. For example, if the SNR is still above the threshold but has been consistently degrading over time, for example, in excess of a predetermined rate, the DSP can output a prompt as user output to perform maintenance or repairs before the system fails.

The DSP outputs a result corresponding to the comparison, according to block 340. For example, as described herein with reference to FIG. 1B, the DSP can send prompts or information indicating whether or not the system performance data meets the predetermined thresholds, or not. The DSP can output prompts for maintenance or replacement of certain parts of the OCT imaging engine, or for example output prompts for further investigation into potential causes of failure or degradation.

In some examples, the DSP can compare system performance data against earlier-generated system performance data. For example, at least some of the times the DSP generates system performance data, for instance according to aspects of the disclosure, the DSP can save the data and later retrieve the data for comparing the data to currently-generated system performance data. Based on the comparison, the DSP can send prompts or information indicating whether differences between the earlier- and currently-generated system performance data vary in excess of a predetermined threshold. Wide variations, for example in excess of 5 percent, can cause the DSP to output a result corresponding to the comparison, according to block 340. As part of the comparison, in some examples the DSP can compare currently generated system performance data to the most recently acquired earlier-generated system performance data, while in other examples the DSP can compare the currently generated system performance data against average metrics computed from a set of earlier-generated system performance data, for example over a period of time. The DSP can also monitor the performance data to identify trends to identify system degradation prior to failure, prompting the user to perform preventive maintenance.

Self-Calibration

In part, the disclosure relates to a calibration process which can calculate the spectra of k-linearization (KL), dispersion, and spectral flattening. The calibration process can provide a set of calibration spectra. OCT signals, including raw fringe data, with a mirror in the sample arm can be acquired from the positive and negative planes separately by adjusting the reference arm path distance.

Calibration spectra can be generated at the calibration stage using a first mirror measurement and a second mirror measurement, the first and second mirror measurement taken when the reference mirror is on opposite sides from a zero-delay line, each mirror measurement being an interferogram or a signal or a system impulse response. Although examples are provided with two mirror measurements, in other examples additional mirror measurements may be used. For example, the calibration may be based on three, four, tens, hundreds, or any number of mirror measurements.

In part, the disclosure relates to utilizing a received calibration spectra to modify or correct an interferogram prior to performing a FFT. The calibration spectra can be used to linearize future fringe data acquired by the system in the wavenumber domain for an improved interferogram. In some examples, wavenumber sampling can be linearized by interpolation using the calibration spectrum (k-linearization). Dispersion can be corrected by applying a Hilbert transform and multiplication with the dispersion spectrum of the k-linearized interferogram.

In part, aspects of the disclosure provide systems and methods that correct not only k-spectrum nonlinearity, but also the dispersion and asymmetric laser sweep intensity separately by using the calibrated spectra with signal processing steps. The disclosure allows for an optimized optical resolution to be maintained across the entire imaging depth. Furthermore, the algorithms, methods, and systems discussed in this disclosure can also work with or without a k-clock providing an option to improve system SNR by using the internal sampling rate of the digitizer, which is typically faster than the maximum frequency of the k-clock.

The system can implement the self-calibration method described herein using optical signals reflected from the reference reflector 286, in conjunction with the interference pattern determined when the optical signal is reflected from the reference mirror at different positions.

The system can implement the self-calibration method described herein using optical signals reflected from the optical connector 188, in conjunction with the interference pattern determined when the optical signal is reflected from a reference mirror at different positions.

The self-calibration process 400A as described herein can be performed, for example, each time the imaging system housing an imaging engine as described herein is powered on, or before beginning an imaging procedure. In other examples, the OCT imaging engine performs the process 400A upon detecting a new or replaced component, such as a new optical connector or joint in the OCT imaging engine. The positions −P1 and P1 are shown on opposite sides of the zero-delay line, but may or may not be equidistant from the zero-delay line. In some examples, positions −P1 and P1 can be equidistant or substantially equidistant to the zero-delay line and in opposite directions relative to the zero-delay line.

Positions −P1 and P1 through P3 are illustrated as examples, but the reference mirror 130 in various examples can be adjusted to different positions relative to the zero-delay line, including the zero-delay line itself. any ordered and finite number of positions can exist. For example, an additional position P4 can exist which is at a greater positive pixel depth than position P3. In an example, the pixel depth can range from +1024 pixels to −1024 pixels.

Aspects of the disclosure provide for performing a calibration process on the OCT imaging engine to measure the PSF of the OCT imaging engine at several positions. The reference reflector 286 can be adjusted, for example, using a motor, to reflect the optical signal at different positions and angles. Through calibration, the OCT imaging engine can maintain performance quality during imaging, while calibrating itself as necessary, without user input. Through calibration as described herein, the OCT imaging engine can also self-correct problems related to the stress-induced dispersion.

The calibration spectra can be used to linearize future fringe data by the system. The wavenumber sampling can be linearized by interpolation using the calibration spectrum (k-linearization) and the dispersion is corrected (DC) by a Hilbert transform. To suppress the sidelobe artifacts caused from the nonuniform laser intensity during a spectral sweep, the spectral envelope of the laser source is flattened to optimize the digitized laser bandwidth. The corrected spectrum is then processed downstream. By correcting the spectrum, the axial resolution can be improved and preserved across the entire depth of the A-scan. No external k-clock is needed.

In part, the disclosure relates to utilizing an obtained calibration spectra to modify or correct an interferogram prior to Fast Fourier Transform (FFT) processing. The calibration spectra can be used to linearize future fringe data acquired by the system in the wavenumber domain for an improved interferogram. In some examples, wavenumber sampling can be linearized by interpolation using the calibration spectrum (k-linearization). Dispersion can be corrected by applying a Hilbert transform and multiplication with the dispersion spectrum of the k-linearized interferogram.

In some examples, the OCT imaging engine can use the reference reflector 286 as part of self-calibration without user input. Aspects of the disclosure provide for performing a calibration process on the OCT imaging engine to measure the PSF of the engine at several positions. The reference reflector 286 can be adjusted, for example, using a motor, to reflect the optical signal at different positions and angles. Alternatively, the reference mirror 130 position can be adjusted to measure the PSF at several positions. Through calibration, the OCT imaging engine can maintain performance quality during imaging, while calibrating itself as necessary, without user input. Through calibration as described herein, the OCT imaging engine can also self-correct problems related to the stress-induced dispersion.

Figure 4A:
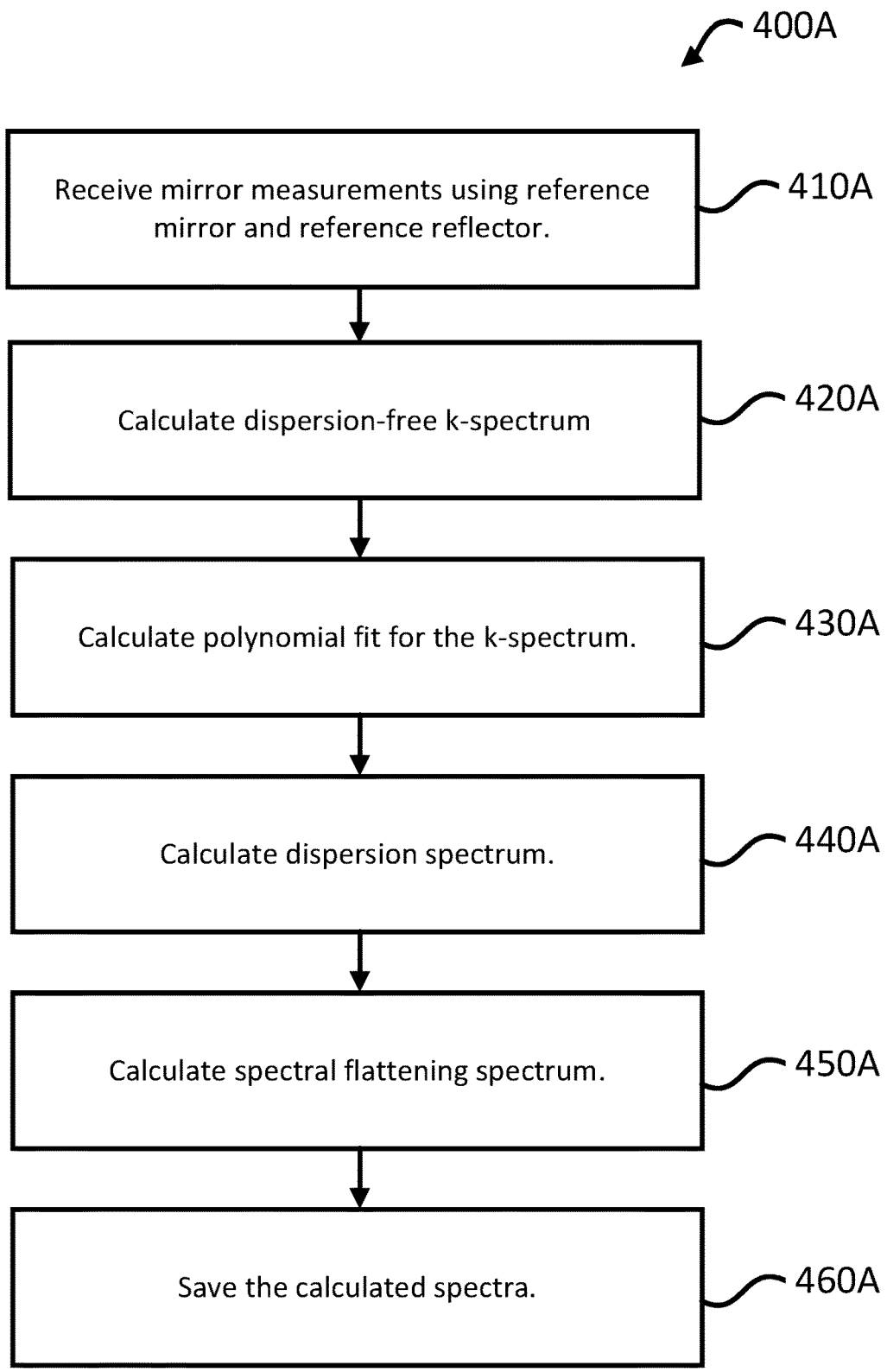
FIG. 4A is a flow chart of an example process for self-calibration using a reference mirror and a reference reflector internal to an OCT imaging engine.

FIG. 4A is a flow chart of an example process 400A for self-calibration using a reference mirror and a reference reflector internal to an OCT imaging engine.

The OCT imaging engine receives mirror measurements using the reference mirror and the reference reflector, according to block 410A. The reference reflector can be the internal reflector shown in FIG. 2C or some other reflection point in the sample arm 135 of the OCT imaging engine such as connection point 192 at the end of the optical connector at the catheter interface 170. A mirror measurement can include a time-varying amplitude of an interferogram. The system can use the received measurements to retrieve the phase of the optical signal as a function of the sampling index n. The optical phase of the received signals can be represented, for example, as $\Phi_{P1}(n)$ and $\Phi_{-P1}(n)$, respectively, where $\Phi_x(n)$ corresponds to the optical phase at position x of the reference mirror 130 (measured, for example, in pixel depth relative to the zero-delay line). The input parameter n is the sampling index of the OCT imaging engine.

As part of receiving the mirror measurements, the OCT imaging engine can receive optical signals from the reference reflector and the reference mirror for respective different positions of the reference mirror. The optical signals received may be referred to as raw fringe data (or, "raw fringe"). The OCT imaging engine can receive multiple optical signals, for example one when the reference mirror is at position P1 as shown and described with reference to FIG. 2B, and another signal when the reference mirror is at position −P1. The positions P1 and −P1 can be any of a variety of pixel depths relative to the zero-delay line of the reference mirror 130. For example, the pixel depths can be 250-300 pixels relative to the zero-delay line, which is equivalent to 25-30% of the Nyquist depth of a 1024-pixel system. In other examples, any two arbitrary positions can be chosen relative to the zero-delay line. The OCT imaging engine can receive mirror measurements for multiple pairs of positions of the reference mirror relative to the zero-delay line. For example, one pair of positions can be (P1, −P1) as described herein, but measurement data for multiple pairs of positions can be received according to block 410A.

The optical signals can include raw fringe data, which can be received when an optical signal is reflected from the reference mirror or the reference reflector when the reference mirror is at different positions with respect to the zero-delay line. A high-pass filter can filter out the low frequency component of the interference signal.

As part of receiving the mirror measurements, the OCT imaging engine can generate interferograms from the received optical signals. For each received optical signal, the OCT imaging engine generates a respective interferogram. The interferograms may be referred to as raw fringe data and may be sampled by the OCT imaging engine using a k-clock.

The engine can apply a Hilbert transform from the generated interferograms to generate a complex signal and phase of the received measurements, for example $\Phi_{P1}(n)$ and $\Phi_{-P1}(n)$. The engine can compute a k-linear phase by averaging the fringe of the optical signal at each measurement, to obtain optical phases $\Phi_{P1}(n)$ and $\Phi_{P2}(n)$.

For example, to compute the optical phase $\Phi_{P1}(n)$ of the received signal at position P1, is observed that the intensity of the signal at position P1 is proportional to a function of the wavenumber of the optical signal, the position of the reference mirror 130 when the signal was received, and the optical dispersion phase of the received optical signal when the reference mirror 130 is at position P1. Example formulations can be:

$$I_{P1}(n) \propto \cos(k(n)Z_{P1} + \Phi_{disp}(n)) \quad (A)$$

$$I_{P1}(n) \propto \cos(k(n)Z_{P2} - \Phi_{disp}(n)) \quad (B)$$

Where $I_{P1}(n)$ corresponds to the intensity of the optical signal received at sampling index n and position P1 of the reference mirror, ∝ means that the left operand (for example $I_{P1}(n)$) is proportional to the right operands (for example cos $(k(n)Z_{P1}+\Phi_{disp}(n)))$, cos (·) is the cosine function, and $k(n)$ is the wavenumber of the received optical signal and $Z_{\pm P1}$ is the mirror distance from the zero delay line.

Using formulas (A) and (B), the OCT imaging engine can perform a Hilbert transform on the received signals to receive the optical phases of the signals at different positions of the reference mirror 130. For example, using a Hilbert transform, the OCT imaging engine can receive $\Phi_{P1}(n)=k(n)Z_{P1}+\Phi_{disp}(n)$ and $\Phi_{P2}(n)=k(n)Z_{P2}-\Phi_{disp}(n)$. The OCT imaging engine can also remove the background from the signals received.

The OCT imaging engine calculates the dispersion-free k-spectrum (k-spectrum) $\Phi_{KL}(n)=0.5*\{(\Phi_{P1}(n)+\Phi_{P1}(n)\}$ according to block 420A. After interpolating the optical fringe by using the KL spectra, the OCT imaging engine can calculate the dispersion spectrum. One example formulation of this relationship for measurement data collected from a pair of reference mirror positions (P1, −P1) is as follows:

$$\Phi_{disp}(n) = \frac{1}{2}((\Phi_{P1}(n)+nX_{P1})-(\Phi_{-P1}(n)+nX_{-P1})) \text{ and} \quad (C)$$

$$X_d = -z_d + \frac{1}{2}(z_{P1}+z_{-P1}),$$

where $d$ can be $P1$ or $-P1$.

For each calibration pair of mirrors, the term $X_d$ is used to compensate the phase difference of the mirror signals from P1 and −P1 due to their unequal positions relative to the zero-delay line. $z_p$ refers to the distance from the zero-delay line.

The OCT imaging engine can calculate a polynomial fitting the k-spectrum $\Phi_{KL}(n)$, according to block 430A. In some examples, to calculate the polynomial, the OCT imaging engine can perform KL resampling with varying polynomial fitting orders using an optical signal acquired while the reference mirror is in different positions, such as P2 or P3. In some examples, the order of the polynomial can vary from zero to fifty, where zero represents the raw k-spectrum without fitting.

The polynomial can be determined based on two or more mirror measurements. A dispersion spectrum or criteria can be calculated for at least one mirror measurement and a compensation can be calculated. A dispersion compensation, dispersion factor, or dispersion criteria can be calculated using two mirror positions with one position on either side of the zero-delay line. Spectral flattening can be performed on at least one mirror measurement by using an envelope calculated from a specific mirror measurement. A spectral envelope calculated during spectral flattening can be saved. Each mirror measurement of the plurality of mirror measurements can be a system impulse response.

In some examples, the OCT imaging engine generates additional interferograms from optical signals received from the reference reflector and the reference mirror while the reference mirror is at positions P1 to P3. The OCT imaging engine can use the additional interferograms to better fit a polynomial and may be used to optimize the k-spectrum based on the best polynomial fitting order detected from the algorithm. In some examples, the locations of P1, P2, and P3 can be chosen based on the desired or estimated depth of a sample to optimize the polynomial fit over the depth range.

As part of calculating the polynomial, the OCT imaging engine can perform one or more iterations of fitting a candidate polynomial of a particular order as described herein and identifying the candidate polynomial order causing the sharpest intensity peak. The polynomial with this identified candidate order can be saved in memory and used during the real-time imaging stage as described herein according to FIG. 4B. The OCT imaging engine can continue searching for an improved polynomial fitting the k-spectrum until meeting one or more convergence criteria, for example a number of iterations, or an amount of time passing since beginning to search.

In some examples, the OCT imaging engine can calculate the full-width-at-half-maximum (FWHM) and the point spread function (PSF) area total based on the PSF profiles after the system performs k-spectrum interpolation by each fitting order. The FWHM and the PSF area total can be calculated for each depth position P1 through P3 for each polynomial order. Afterward, the system can average and normalize the FWHM and PSF area total for each position.

Using the averaged FWHM and PSF area total from multiple, for example, three different depths, the system can search for a polynomial order applied on KL spectra to have a minimum FWHM and PSF across depths.

The OCT imaging engine calculates the dispersion spectrum, according to block 440A. The OCT imaging engine interpolates raw fringe data using the k-spectrum and polynomial calculated according to blocks 410A-430A. The dispersion phase $\Phi_{disp}(n)$ can be calculated according to formula C, described herein. The OCT imaging engine can remove the noise appearing in the dispersion spectrum by fitting the spectrum with a polynomial function or applying a low pass filter. The dispersion phase function $\Phi_{disp}(k)$ can be saved and used as a counter-dispersive phase to subtract from the analytical form of the KL-corrected fringe.

The OCT imaging engine calculates the spectral flattening spectrum, according to block 450A. The OCT imaging engine can calculate the spectral flattening spectrum using fringe data corrected using the k-spectrum and the dispersion spectrum, calculated according to blocks 420A-440A. In some examples, spectral flattening can further increase the axial resolution of an output image by increasing available bandwidth. For example, the OCT imaging engine can calculate a spectral flattening window as a calibration step and apply the window to future data using a window function, such as a Kaiser-Bessel window. Using the window function, the OCT imaging engine can form a demodulation window, for example $$s_2(n) = s_1(n) \times \frac{\text{kaiser window}}{SF(n)}, \text{ where } s_1(\cdot)$$

is fringe data is corrected using the k-spectrum and the dispersion spectrum. In some examples, the envelope used can be derived from optical signals received from the reference reflector and any of the reference mirror positions. In some examples, as part of calculating the spectral flattening spectrum, the OCT imaging engine calculates the envelope of fringe data by taking the absolute value of the k-spectrum and dispersion spectrum-corrected fringe after applying a Hilbert transform.

The OCT imaging engine saves one or more of the k-spectrum, the polynomial calculated to fit the k-spectrum, the dispersion spectrum, and the spectral flattening spectra are saved, according to block 460A. Collectively, the saved spectra are referred to as calibration spectra.

Figure 4B:
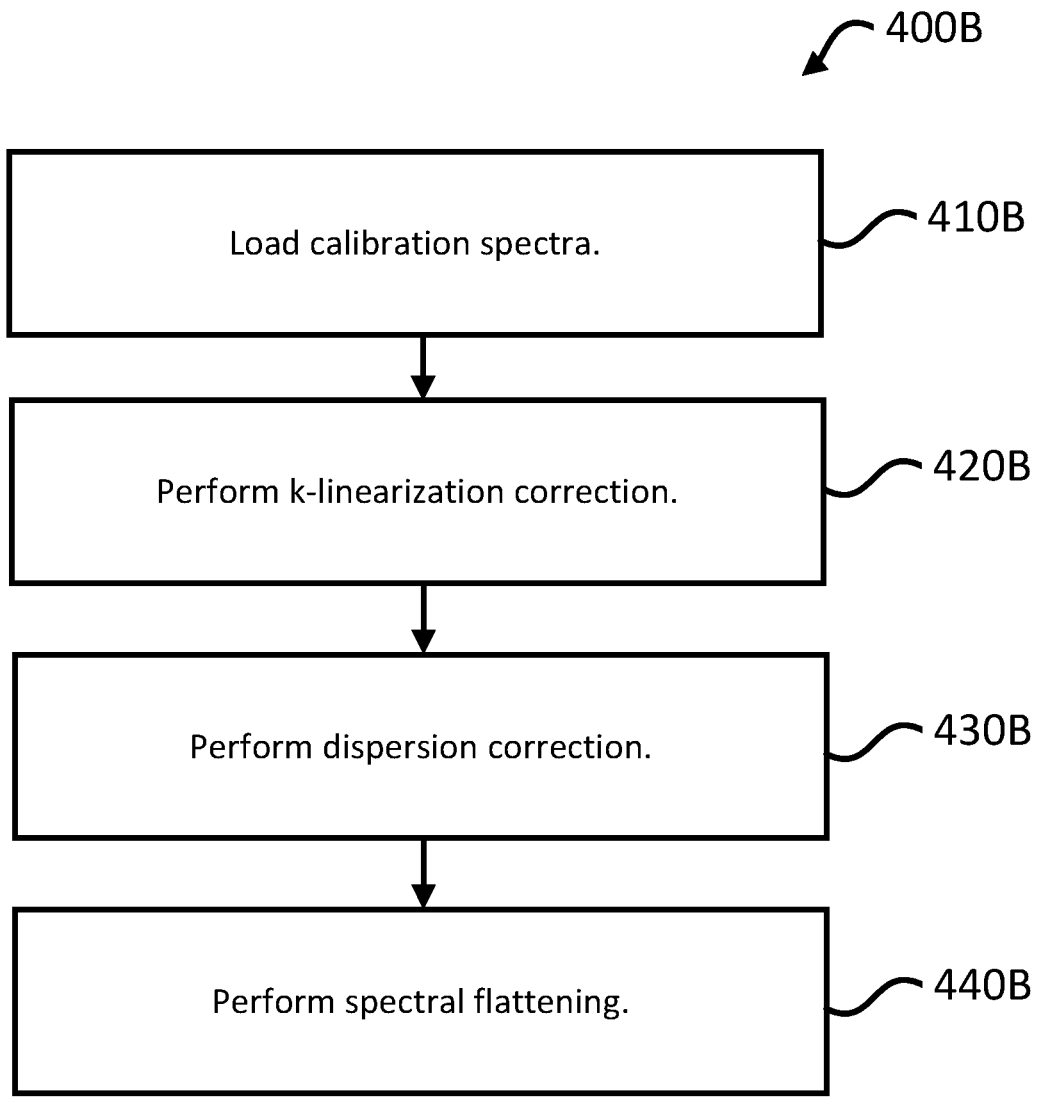
FIG. 4B is a flow diagram for a self-calibration process performed by the OCT imaging engine, according to aspects of the disclosure.

FIG. 4B is a flow diagram for a self-calibration process 400B performed by the OCT imaging engine, according to aspects of the disclosure.

The OCT imaging engine receives one or more calibration spectra, according to block 410B. For example, the calibration spectra can be previously calculated by the OCT imaging engine and saved, as described herein with reference to FIG. 4A.

The OCT imaging engine receives optical signals, and while receiving the optical signals, performs k-linearization correction, according to block 420B. To perform k-linearization correction, the OCT imaging engine can interpolate the incoming optical signals using the saved k-spectrum and the polynomial fitting order.

In some examples, the OCT imaging engine can perform a cubic spline interpolation in the wavenumber space (k-space) on the received optical data. Performing a cubic spline interpolation in the wavenumber space can allow for scaling the raw fringe data from a nonlinear domain to a linear wavenumber domain, prior to performing an FFT process.

Spline interpolation is a form of piecewise polynomial interpolation to avoid overfitting, which can cause spike errors. In some examples, accelerators such as field-programmable gate arrays (FPGAs), graphics processing units (GPUs), or application-specific integrated circuits (ASICs) can be used to accelerate the cubic spline interpolation in the wavenumber domain, allowing the correction to be performed in real-time and during operation of the OCT imaging engine.

According to block 430B, the OCT imaging engine performs dispersion correction on the fringe data. The OCT imaging engine applies a saved dispersion spectrum, for example generating according to block 440A of the process 400A of FIG. 4A. The OCT imaging engine performs dispersion compensation to cancel out the dispersion phase and correct the optical signal being received. In examples in which a polynomial-fitted function or low pass filter is applied to the optical signal, a more robust correction can be performed as compared with dispersion correction on un-corrected fringe data.

For example, the OCT imaging engine can apply a Hilbert transform on the raw fringe data to convert the data into an analytical form. The OCT imaging engine can compensate for the dispersion phase by using an exponential function of the dispersion spectrum. An example formulation of the exponential function is $=j\Phi_{disp}(n)$, where j is an imaginary unit.

The OCT imaging engine can compute a new fringe function by taking the real part of the corrected fringe data, multiplied by the complex-valued phase. An example formulation of the fringe function can be:

$$s_1(n)=\text{Real}\{\text{analytical form of } s_0(n) \times \exp[-j\Phi_{disp}(n)]\} \quad (D)$$

where $s_1(n)$ is the new fringe function and $s_0(n)$ is the optical signal with k-spectrum correction. The real function referred to in equation (D) takes the real-valued portion of the fringe data that has been k-linearized and transformed to the complex-valued analytical form.

The OCT imaging engine applies spectral flattening to the k-linearized and dispersion-corrected signal, according to block 440B. Spectral flattening can be performed on at least one mirror measurement by using an envelope calculated from a specific mirror measurement. Each mirror measurement of the plurality of mirror measurements can be a system impulse response. Dispersion compensation can be calculated for at least one mirror measurement. A dispersion spectrum or criterion can be calculated for at least one mirror measurement and a compensation can be calculated. A dispersion compensation, dispersion factor, or dispersion criteria can be calculated using two mirror positions which are symmetric across a zero-delay line. A spectral envelope calculated during spectral flattening can be saved.

In some examples, spectral flattening can further increase the performance of the axial resolution by increasing the available bandwidth. In one example a spectral flattening window can be calculated as a calibration step and applied to future data using a window function (e.g., Kaiser-Bessel window) to form a demodulation window. The envelope used can be derived from the signal obtained from any of reference mirror positions from block 305.

In one example, the first step of the spectral flattening process is to calculate the envelope of the fringe by taking the absolute value of the KLDC-corrected fringe after a Hilbert transform has been applied to it. This step can occur when a mirror is placed in the sample arm. Upon calculation of the spectral envelope, the spectral envelope can be fitted by a polynomial function.

The processes 400A and 440B can be repeated multiple times before, while, or after one of the OCT imaging engines 100A-F is in operation. For example, the OCT imaging engine 100 may perform the process 300 to obtain quantifying information from PSF received from the reference reflector when the OCT imaging engine is first powered on. In addition, or alternatively, the OCT imaging engine can perform the process 400A periodically, or in response to user input requesting self-assessment and calibration. The input may be, for example, receiving input by the OCT imaging engine to change the position of a switch, causing the OCT imaging engine to operate in catheter connection check mode and measure the reflected loss for the back reflection of an optical signal.

Figure 5A:
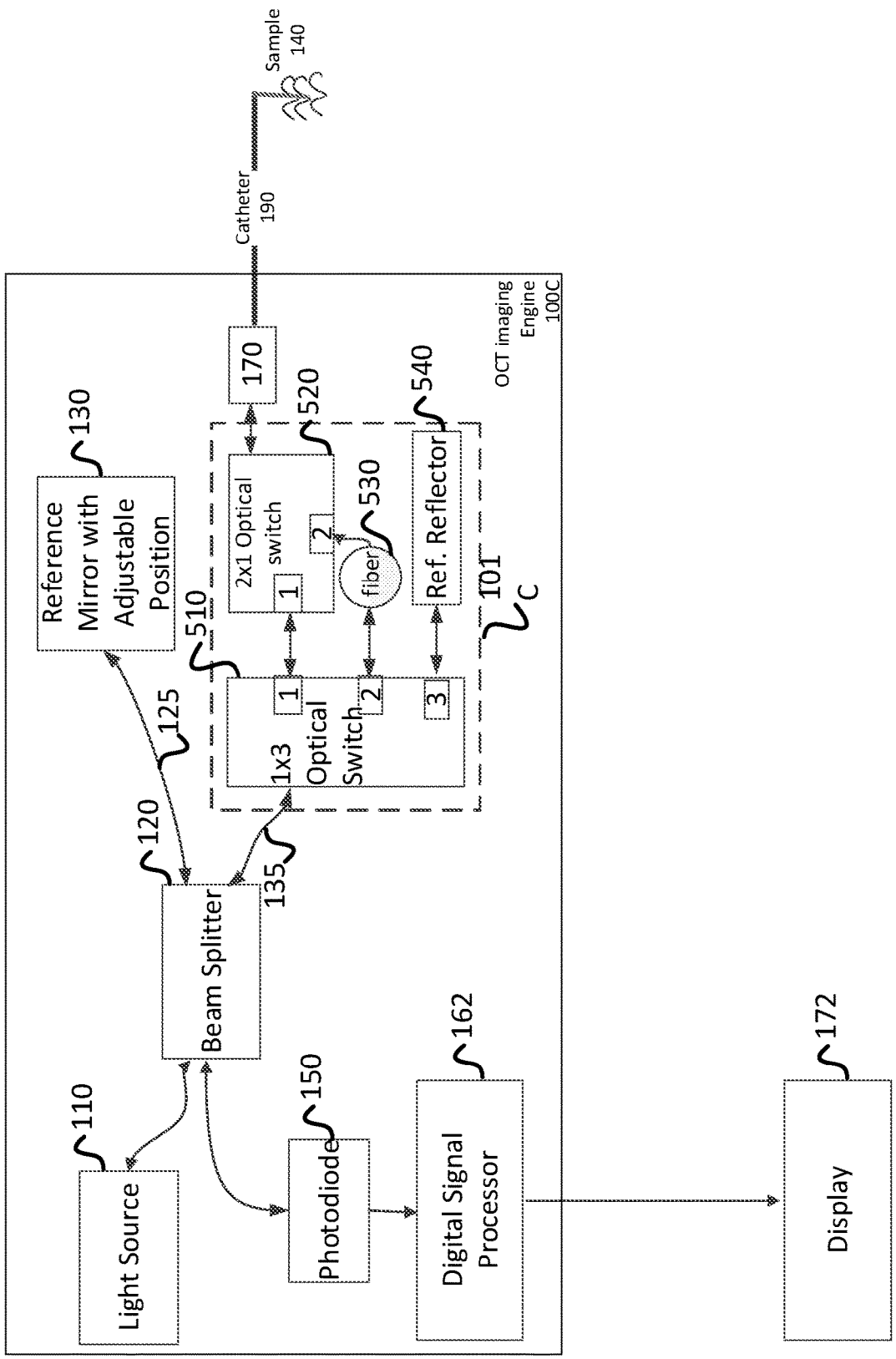
FIG. 5A is an example OCT imaging engine for performing both catheter connection checking and self-assessment and calibration, according to aspects of the disclosure.
Figure 5B:
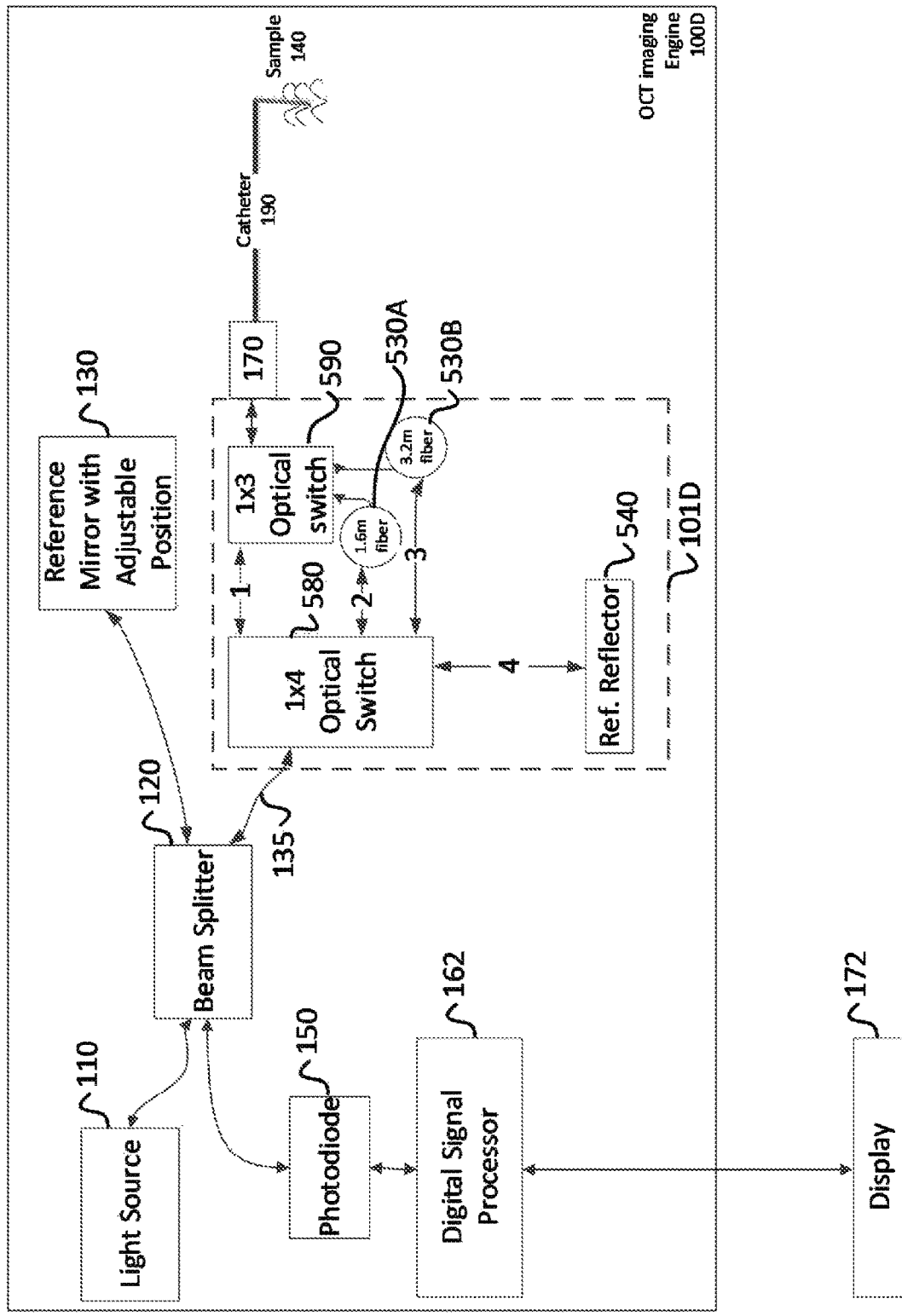
FIG. 5B is a block diagram of an example OCT imaging engine for performing both catheter connection checking and self-assessment and calibration and configured for dual catheter lengths.

FIG. 5A is a block diagram of an example OCT imaging engine 100C for performing both catheter connection checking and self-assessment and calibration, according to aspects of the disclosure. The OCT imaging engine 100C can be configured to be able to operate in either catheter connection check mode, or in self-assessment and calibration mode. The OCT imaging engine 100C can include a combined catheter connection check and self-assessment/calibration engine 101C.

The OCT imaging engine 100C includes a 1×3 optical switch 510, a 2×1 optical switch 520, fiber optic cable 530, and a reference reflector 540. The optical switches 510, 520 and the fiber optic cable 530 can be in sample arm 135 of the OCT imaging engine 100C. The 2×1 optical switch 520 and the fiber optic cable 530 can be implemented, for example, as described with reference to the optical switch 160 and the fiber optic cable 184 of FIG. 1A. Instead of connecting directly with the beam splitter 120, the 2×1 optical switch 520 connects to the 1×3 optical switch 510.

When the switches 510, 520 are in a first position, the switches 510, 520 cause an optical signal to pass to and from the beam splitter 129 and the catheter interface 170. When the switches 510, 520 are in the first position, the OCT imaging engine 100C can be said to be in operation to measure optical signals and to generate corresponding tomograms or other images using the measured optical signals.

When the switches 510, 520 are in a second position, the switches 510, 520 cause optical signals to pass through the fiber optic cable 530. As described herein with reference to the DSP 162 of FIG. 1A, the DSP 162 of FIG. 1A can be configured to receive the reflected loss of the back reflection of the optical signal through an optical connector connection point between the catheter interface 170 and the catheter 190. The DSP 162 can determine whether the connection is successful or not based on a comparison between the reflected loss and a predetermined threshold, as described with reference to FIGS. 1B-1C.

When the switch 510 is in a third position, the switch 510 causes the optical signal to pass through the reference reflector 286. As described herein with reference to the DSP 162 and the reference reflector 540, the DSP 162 can receive PSF from the reference reflector 540. The DSP 162 can process the PSF, as described herein with reference to FIG. 3, and generate information quantifying the performance of the OCT imaging engine 100C.

In some examples, the OCT imaging engine 100C may be connected to one or more storage devices configured for storing information measured and generated by the OCT imaging engine 100C while in operation, either in catheter connection check mode, self-assessment and calibration mode, or both catheter connection check and self-assessment and calibration mode.

FIG. 5B is a block diagram of an example OCT imaging engine 100D for performing both catheter connection checking and self-assessment and calibration and configured for dual catheter lengths. The OCT imaging engine 100D can include a combined catheter connection check and self-assessment/calibration engine 101D.

As shown in FIG. 5B, the OCT imaging engine 100D can include variable length fibers 530A and 530B. In one example, the lengths of fibers 530A and 530B can be 1.6 and 3.2 meters, respectively, although in other examples the lengths can be longer or shorter. Having multiple fiber lengths available allows the OCT imaging engine 100D to perform catheter checks on different lengths of catheters. To accommodate for different potential fiber lengths, the OCT imaging engine 100D can implement a 1×4 optical switch 580 and a 1×3 optical switch 590. The sizes of the optical switches can vary depending on the number of fibers available in the OCT imaging engine 101D.

Figure 5C:
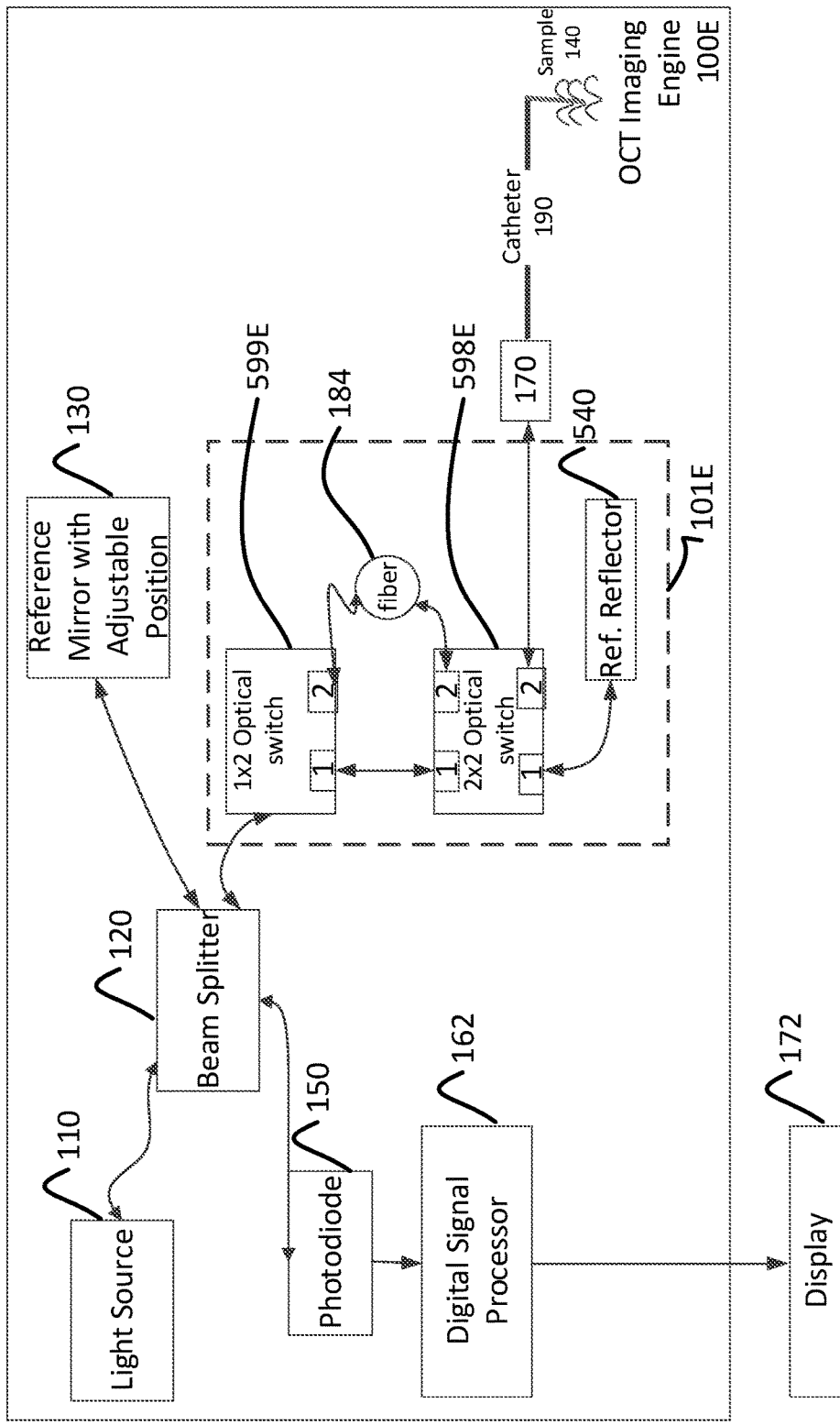
FIG. 5C is a block diagram of an example OCT imaging engine using a 1×2 and a 2×2 switch for performing both catheter connection checking and self-assessment and calibration, according to aspects of the disclosure.

FIG. 5C is a block diagram of an example OCT imaging engine 100E using a 1×2 and a 2×2 switch for performing both catheter connection checking and self-assessment and calibration, according to aspects of the disclosure. The OCT imaging engine 100E can include a combined catheter connection check and self-assessment/calibration engine 101E. As shown in FIG. 5C, the OCT imaging engine 100E can include a 1×2 optical switch 599E and a 2×2 optical switch 598E. As described herein with reference to FIGS. 5A-D, the quantity and types of optical switches can vary from example to example.

Figure 5D:
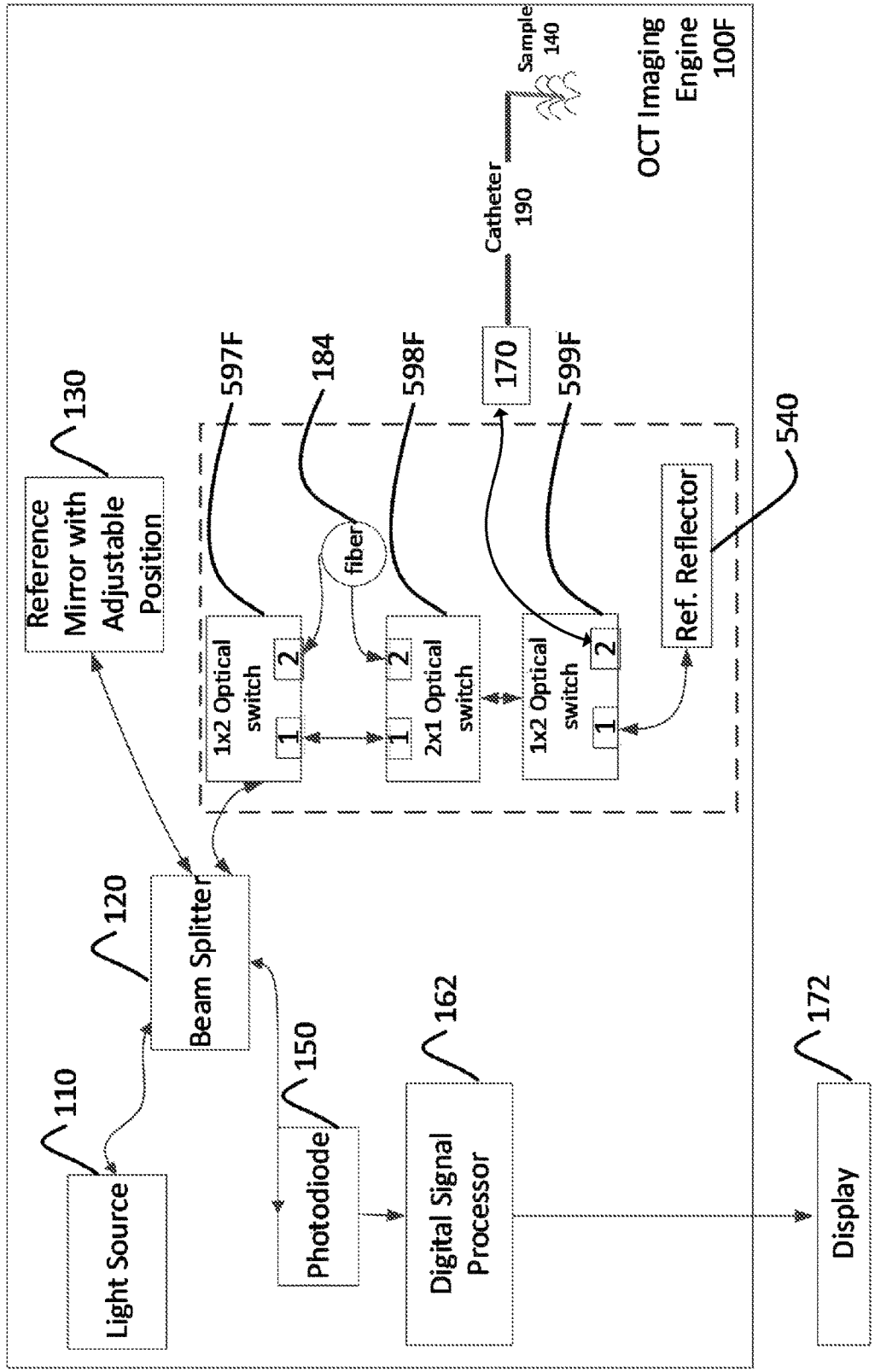
FIG. 5D is a block diagram of an example OCT imaging engine using two 1×2 optical switches and one optical switch for performing both catheter connection checking and self-assessment and calibration, according to aspects of the disclosure.

FIG. 5D is a block diagram of an example OCT imaging engine 100F using two 1×2 optical switches 597E, 598E and one 2×1 optical switch 599E for performing both catheter connection checking and self-assessment and calibration, according to aspects of the disclosure. The OCT imaging engine 100F can include a combined catheter connection check and self-assessment/calibration engine 101F. As shown in FIG. 5D, the OCT imaging engine 100F can include two 1×2 optical switches 597F, 598E connected through a 2×2 optical switch 599E.

Figure 6:
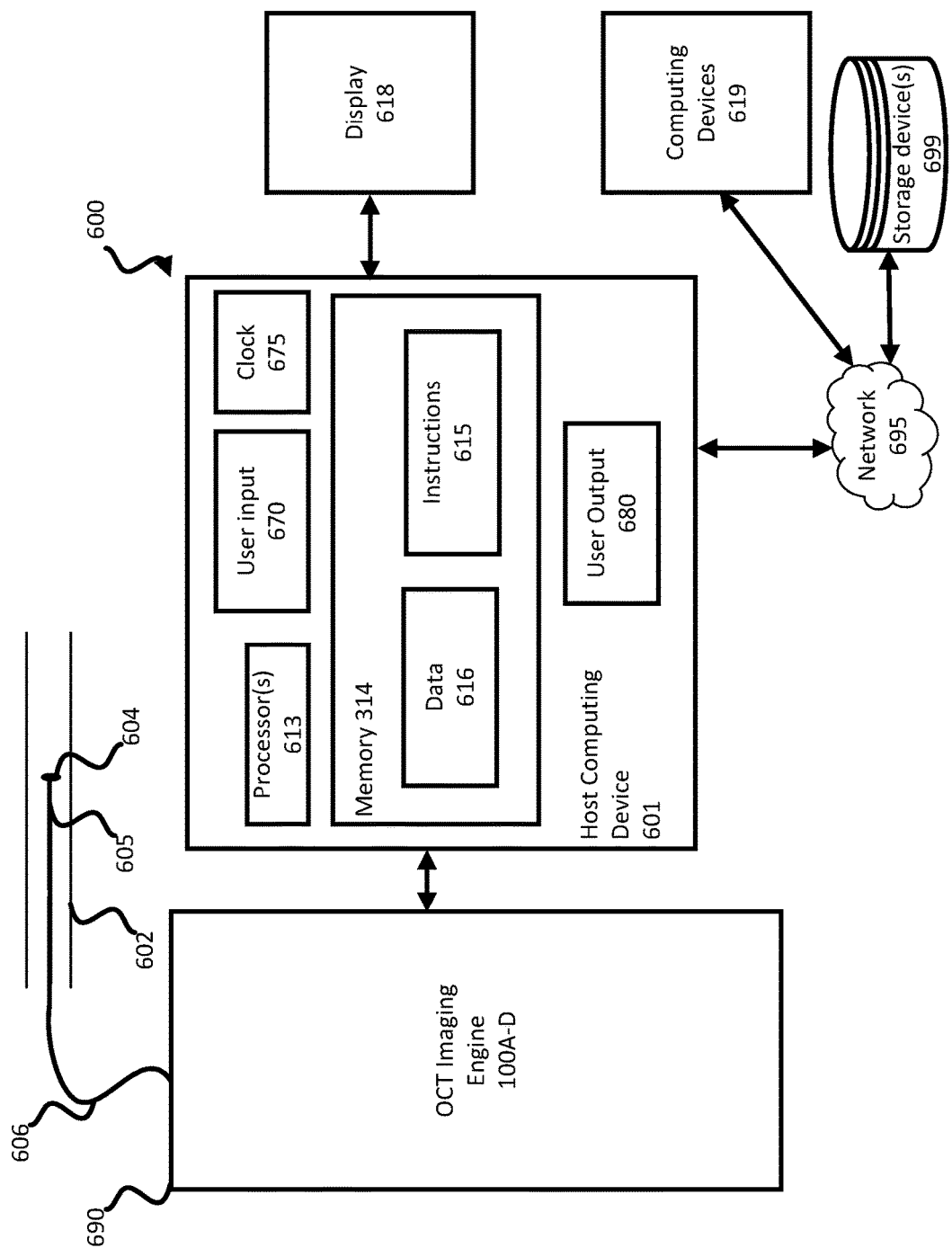
FIG. 6 is a block diagram of an imaging environment including the OCT imaging engine and a host computing device.

FIG. 6 is a block diagram of an imaging environment 600 including one or more of the OCT imaging engines 100A-F and a host computing device 601. The host computing device ("host device") 601 can include one or more processors configured for receiving signals from various types of imaging devices, and processing the signals to generate one or more image frames or other visual data corresponding to the received signals.

The host device 601 can include a user input 670. The user input 670 can include any appropriate mechanism or technique for receiving input from a user, such as keyboard, mouse, mechanical actuators, soft actuators, touchscreens, microphones, and sensors.

The host device 601 can be configured to receive an image from an imaging device 605 having an imaging probe 604. The imaging probe 604 may be an OCT probe and/or an IVUS catheter, as examples. A guidewire, not shown, may be used to introduce the probe 604 into a blood vessel 602, for example a blood vessel of the target 607. The probe 604 may be introduced and pulled back along a length of a lumen of the blood vessel 602 while collecting data, for example as a sequence of image frames. According to some examples, the probe 604 may be held stationary during a pullback such that a plurality of scans of data sets may be collected.

The probe 604 may be connected to the user computing device 601 through an optical fiber 606. The host device 601 may include a light source, such as a laser, an interferometer having a sample arm and a reference arm, various optical paths, a clock generator, photodiodes, and other OCT components. In some examples, the host device 601 is connected to one or more other devices and/or pieces of equipment (not shown) configured for performing medical imaging using one of the OCT imaging engines 100A-F. As an example, the host device 601 and one of the imaging engine 100A-F can be part of a catheterization lab.

The probe 604 may be connected to an optical receiver 665. According to some examples, the optical receiver 665 may be a balanced photodiode-based system. The optical receiver 665 may be configured to receive light collected by the probe 604.

The host device 601 can be communicatively coupled to one or more storage devices 690 or computing device(s) 619 over a network 695. The storage device(s) 699 or computing device(s) 619 can be a combination of volatile and non-volatile memory, and can be at the same or different physical locations as the host device 601 and/or OCT imaging engine 100A-D. For example, the storage device(s) 690 can include any type of non-transitory computer readable medium capable of storing information, such as a hard-drive, solid state drive, tape drive, optical storage, memory card, ROM, RAM, DVD, CD-ROM, write-capable, and read-only memories.

The host device 601 can include one or more processors 613 and memory 614. The memory 614 can store information accessible by the processor(s) 613, including instructions 615 that can be executed by the processor(s) 613. The memory 614 can also include data 616 that can be retrieved, manipulated or stored by the processor(s) 613. The memory 614 can be a type of non-transitory computer readable medium capable of storing information accessible by the processor(s) 613, such as volatile and non-volatile memory. The processor(s) 613 can include one or more central processing units (CPUs), graphic processing units (GPUs), field-programmable gate arrays (FPGAs), and/or application-specific integrated circuits (ASICs).

The instructions 615 can include one or more instructions that when executed by the processor(s) 613, causes the one or more processors to perform actions defined by the instructions. The instructions 615 can be stored in object code format for direct processing by the processor(s) 613, or in other formats including interpretable scripts or collections of independent source code engines that are interpreted on demand or compiled in advance.

The data 616 can be retrieved, stored, or modified by the processor(s) 613 in accordance with the instructions 615. The data 616 can be stored in computer registers, in a relational or non-relational database as a table having a plurality of different fields and records, or as JSON, YAML, proto, or XML documents. The data 616 can also be formatted in a computer-readable format such as, but not limited to, binary values, ASCII or Unicode. Moreover, the data 616 can include information sufficient to identify relevant information, such as numbers, descriptive text, proprietary codes, pointers, references to data stored in other memories, including other network locations, or information that is used by a function to calculate relevant data.

The host device 601 can be configured to display at least a portion of the received data on a display implemented as part of the user output 680. The user output 680 can also be used for displaying an interface host device 601 on the display 618. The user output 680 can alternatively or additionally include one or more speakers, transducers or other audio outputs, a haptic interface or other tactile feedback that provides non-visual and non-audible information to a user of the host device 601.

Although FIG. 6 illustrates the processor(s) 613 and the memory 614 as being within the host device 601, components described in this specification, including the processor(s) 613 and the memory 614, can include multiple processors and memories that can operate in different physical locations and not within the same computing device. For example, some of the instructions 615 and the data 616 can be stored on a removable SD card and others within a read-only computer chip. Some or all of the instructions and data can be stored in a location physically remote from, yet still accessible by, the processor(s) 613. Similarly, the processor(s) 613 can include a collection of processors that can perform concurrent and/or sequential operation. The host device 601 can each include one or more internal clocks providing timing information, which can be used for time measurement for operations and programs run by the host device 601. In some examples, the host device 601 is physically remote from imaging equipment from which image data or image frames are received. The host device 601 can be configured to receive temporal data, image frames, and/or other data over the network 695.

The host device 601 can be capable of direct and indirect communication with one or more other devices over the network 695. The host device 601 can set up listening sockets that may accept an initiating connection for sending and receiving information. The network 695 itself can include various configurations and protocols including the Internet, World Wide Web, intranets, virtual private networks, wide area networks, local networks, and private networks using communication protocols proprietary to one or more companies. The network 695 can support a variety of short- and long-range connections. The short- and long-range connections may be made over different bandwidths, such as 2.402 GHz to 2.480 GHz (commonly associated with the Bluetooth® standard), 2.4 GHz and 5 GHz (commonly associated with the Wi-Fi® communication protocol); or with a variety of communication standards, such as the LTE® standard for wireless broadband communication. The network 695, in addition or alternatively, can also support wired connections between the host device 601, the OCT imaging engines 100A-F, and/or other computing devices, including over various types of Ethernet connection.

Although a single host device 601 and OCT imaging engine 100A-F are shown in FIG. 6B, it is understood that the aspects of the disclosure can be implemented according to a variety of different configurations and quantities of devices, including paradigms for sequential or parallel processing, or over a distributed network of multiple devices. In some implementations, aspects of the disclosure can be performed on a single device, and any combination thereof.

Computer program logic implementing all or part of the functionality previously described herein may be embodied in various forms, including, but in no way limited to, a source code form, a computer executable form, and various intermediate forms (e.g., forms generated by an assembler, compiler, linker, or locator). Source code may include a series of computer program instructions implemented in any of various programming languages (e.g., an object code, an assembly language, or a high-level language such as Fortran, C, C++, JAVA, or HTML) for use with various operating systems or operating environments. The source code may define and use various data structures and communication messages. The source code may be in a computer executable form (e.g., via an interpreter), or the source code may be converted (e.g., via a translator, assembler, or compiler) into a computer executable form.

The computer program may be fixed in any form (e.g., source code form, computer executable form, or an intermediate form) either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCMCIA card), or other memory device. The computer program may be fixed in any form in a signal that is transmittable to a computer using any of various communication technologies, including, but in no way limited to, analog technologies, digital technologies, optical technologies, wireless technologies (e.g., Bluetooth), networking technologies, and internetworking technologies. The computer program may be distributed in any form as a removable storage medium with accompanying printed or electronic documentation (e.g., shrink-wrapped software), preloaded with a computer system (e.g., on system ROM or fixed disk), or distributed from a server or electronic bulletin board over the communication system (e.g., the Internet or World Wide Web).

Hardware logic (including programmable logic for use with a programmable logic device) implementing all or part of the functionality previously described herein may be designed using traditional manual methods, or may be designed, captured, simulated, or documented electronically using various tools, such as Computer Aided Design (CAD), a hardware description language (e.g., VHDL or AHDL), or a PLD programming language (e.g., PALASM, ABEL, or CUPL).

Programmable logic may be fixed either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), or other memory device. The programmable logic may be fixed in a signal that is transmittable to a computer using any of various communication technologies, including, but in no way limited to, analog technologies, digital technologies, optical technologies, wireless technologies (e.g., Bluetooth), networking technologies, and internetworking technologies. The programmable logic may be distributed as a removable storage medium with accompanying printed or electronic documentation (e.g., shrink-wrapped software), preloaded with a computer system (e.g., on system ROM or fixed disk), or distributed from a server or electronic bulletin board over the communication system (e.g., the Internet or World Wide Web).

Various examples of suitable processing engines are discussed below in more detail. As used herein an engine or system can refer to software, hardware, and/or firmware suitable for performing a specific data processing or data transmission task. In some examples, an engine or system can refer to a software routine, program, or other memory resident application suitable for receiving, transforming, routing, and processing instructions, or various types of data such as OCT scan data and other information of interest.

In this specification the phrase "configured to" is used in different contexts related to computer systems, hardware, or part of a computer program, engine, or module. When a system is said to be configured to perform one or more operations, this means that the system has appropriate software, firmware, and/or hardware installed on the system that, when in operation, causes the system to perform the one or more operations. When some hardware is said to be configured to perform one or more operations, this means that the hardware includes one or more circuits that, when in operation, receive input and generate output according to the input and corresponding to the one or more operations. When a computer program, engine, or module is said to be configured to perform one or more operations, this means that the computer program includes one or more program instructions, that when executed by one or more computers, causes the one or more computers to perform the one or more operations.

Computers and computer systems described herein may include operatively associated computer-readable media such as memory for storing software applications used in obtaining, processing, storing and/or communicating data. It can be appreciated that such memory can be internal, external, remote or local with respect to its operatively associated computer or computer system.

In general, computer-readable memory media applied in association with implementations of the disclosure described herein may include any memory medium capable of storing instructions executed by a programmable apparatus. Where applicable, method steps described herein may be embodied or executed as instructions stored on a computer-readable memory medium or memory media. These instructions may be software embodied in various programming languages such as C++, C, Java, and/or a variety of other kinds of software programming languages that may be applied to create instructions in accordance with implementations of the disclosure.

A storage medium may be non-transitory or include a non-transitory device. Accordingly, a non-transitory storage medium or non-transitory device may include a device that is tangible, meaning that the device has a concrete physical form, although the device may change its physical state. Thus, for example, non-transitory refers to a device remaining tangible despite this change in state.

The aspects, implementations, features, and examples of the disclosure are to be considered illustrative in all respects and are not intended to limit the disclosure, the scope of which is defined only by the claims. Other implementations, modifications, and usages will be apparent to those skilled in the art without departing from the spirit and scope of the claimed disclosure.

The use of headings and sections in the application is not meant to limit the disclosure; each section can apply to any aspect, implementation, or feature of the disclosure Throughout the application, where compositions are described as having, including, or comprising specific components, or where processes are described as having, including or comprising specific process steps, it is contemplated that compositions of the present teachings also consist essentially of, or consist of, the recited components, and that the processes of the present teachings also consist essentially of, or consist of, the recited process steps.

In the application, where an element or component is said to be included in and/or selected from a list of recited elements or components, it should be understood that the element or component can be any one of the recited elements or components and can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein.

The use of the terms "include," "includes," "including," "have," "has," or "having" should be generally understood as open-ended and non-limiting unless specifically stated otherwise.

The use of the singular herein includes the plural (and vice versa) unless specifically stated otherwise. Moreover, the singular forms "a," "an," and "the" include plural forms unless the context clearly dictates otherwise. In addition, where the use of the term "about" or "substantially" is before a quantitative value, the present teachings also include the specific quantitative value itself, unless specifically stated otherwise. The terms "about" and "substantially" as used herein, refer to variations in a numerical quantity that can occur, for example, through measuring or handling procedures in the real world; through inadvertent error in these procedures; through differences/faults in the manufacture of materials, such as composite tape, through imperfections; as well as variations that would be recognized by one in the skill in the art as being equivalent so long as such variations do not encompass known values practiced by the prior art. Typically, the terms "about" and "substantially" means greater or lesser than the value or range of values stated by $\frac{1}{10}$ of the stated value, e.g., ±10%.

It should be understood that the order of steps or order for performing certain actions is immaterial so long as the present teachings remain operable. Moreover, two or more steps or actions may be conducted simultaneously.

It is to be understood that the figures and descriptions of the disclosure have been simplified to illustrate elements that are relevant for a clear understanding of the disclosure, while eliminating, for purposes of clarity, other elements. Those of ordinary skill in the art will recognize, however, that these and other elements may be desirable. However, because such elements are well known in the art, and because they do not facilitate a better understanding of the disclosure, a discussion of such elements is not provided herein. It should be appreciated that the figures are presented for illustrative purposes and not as construction drawings. Omitted details and modifications or alternative implementations are within the purview of persons of ordinary skill in the art.

It can be appreciated that, in certain aspects of the disclosure, a single component may be replaced by multiple components, and multiple components may be replaced by a single component, to provide an element or structure or to perform a given function or functions. Except where such substitution would not be operative to practice certain implementations of the disclosure, such substitution is considered within the scope of the disclosure.

The examples presented herein are intended to illustrate potential and specific implementations of the disclosure. It can be appreciated that the examples are intended primarily for purposes of illustration of the disclosure for those skilled in the art. There may be variations to these diagrams, or the operations described herein without departing from the spirit of the disclosure. For instance, in certain cases, method steps or operations may be performed or executed in differing order, or operations may be added, deleted, or modified.

Although the disclosure relates to different aspects and implementations and other features as recited and depicted herein, it is understood that each of the foregoing disclosed herein can be integrated together as a whole or in part, as appropriate. Thus, each implementation disclosed herein can be incorporated in each of the aspects to varying degrees as appropriate for a given implementation. Further, the various methods and techniques described herein can be used with various imaging modalities.

The invention claimed is:

1. An imaging system comprising:
    a light source adapted to be coupled to a first optical connector;
    a catheter adapted to be coupled to a second optical connector, and adapted to be coupled to the light source using the first optical connector and the second optical connector;
    an interferometer comprising a plurality of optical switches,
        at least two of the plurality of optical switches connected together by a length of optical fiber,
        when in a first position, the plurality of optical switches create a first optical path for optical signals to pass to and from the light source and the catheter, and
        when in a second position, the plurality of optical switches create a second optical path for optical signals to pass to and from a light source along the length of optical fiber; and
    one or more processors configured to perform operations comprising:
        receiving a back reflection of an optical signal at a connection point between the first and second optical connectors; and
        determining, based on the back reflection, whether the catheter is fully connected or not fully connected to the light source.

2. The system of claim 1,
    wherein in determining, based on the back reflection, whether the catheter is fully or not fully connected to the light source, the one or more processors are further configured to perform operations comprising:
    calculating a return loss of the back reflection; and
    determining whether the catheter is fully connected or not fully connected to the light source based on a comparison between the calculated return loss and a predetermined return loss threshold.

3. The system of claim 2, wherein the one or more processors are further configured to perform operations comprising:
    in response to the determination that the catheter is not fully connected, performing one or more of:
        outputting a prompt or signal indicating a potential issue with the catheter, and
        outputting data characterizing a quality of the physical connection between the catheter and the light source.

4. The system of claim 2, wherein the one or more processors are further configured to perform operations comprising:
    in response to the determination that the catheter is fully connected, performing one or more of:
        outputting a prompt or signal indicating that the catheter is fully connected, and
        outputting data characterizing a quality of the physical connection between the catheter and the light source.

5. The system of claim 1,
    wherein the interferometer comprises a reference reflector coupled to a third optical switch of the plurality of optical switches, and wherein the one or more processors are further configured to perform operations comprising:
    receiving an optical signal reflected by the reference reflector; and
    calculating system performance data, comprising one or more of:
        point spread function,
        noise level,
        signal-to-noise ratio, or
        dynamic range.

6. The system of claim 5, wherein the one or more processors are further configured to perform operations comprising:
    comparing the system performance data against one or more predetermined thresholds; and
    outputting a result corresponding to the comparison.

7. The system of claim 5, wherein the one or more processors are further configured to perform operations comprising:
    comparing the system performance data against system performance data generated at an earlier point in time; and
    outputting a result corresponding to the comparison.

8. The system of claim 5, wherein the one or more processors are configured to:
    determine that the system has been powered on; and
    receive the optical signal and calculate the system performance data in response to determining that the system has powered on.

9. The system of claim 1,
    wherein the interferometer comprises a reference reflector coupled to a third optical switch of the plurality of optical switches, and wherein the one or more processors are further configured to perform operations comprising:
    receiving one or more mirror measurements using the reference reflector and a reference mirror;
    performing, using the one or more mirror measurements, one or more of:
        calculating a dispersion-free k-spectrum;
        calculating a polynomial fit for the dispersion-free k-spectrum;
        calculating a dispersion spectrum; or
        calculating a spectral-flattening spectrum; and
    saving one or more of the calculated spectra and the polynomial fit as calibration spectra to memory.

10. The system of claim 9, wherein the one or more mirror measurements comprise a plurality of mirror measurements taken from the reference reflector positioned on either side of a zero-delay line.

11. The system of claim 9, wherein the one or more processors are further configured to perform operations comprising:
  loading the calibration spectra; and
  performing, using the loaded calibration spectra, one or more of: k-linearization, dispersion correction, or spectral flattening.

12. The system of claim 1, wherein the one or more processors are further configured to perform operations comprising:
  receiving the back reflection of the optical signal at the connection point while the catheter is not connected to the light source; and
  determining, based on a return loss for the back reflection of the optical signal at the connection point while the catheter is not connected to the light source, whether the connection point is degraded.

13. An imaging system comprising:
  a light source adapted to be coupled to a first optical connector;
  a catheter adapted to be coupled to a second optical connector, the catheter adapted to be coupled to the light source using the first optical connector and the second optical connector;
  an interferometer comprising one or more optical switches and a reference reflector coupled to a first optical switch of one or more optical switches; and
  one or more processors configured to perform operations comprising:
    receiving an optical signal reflected by the reference reflector;
    calculating system performance data, comprising one or more of:
      point spread function,
      noise level,
      signal-to-noise ratio, or
      dynamic range;
    receiving one or more mirror measurements using the reference reflector and a reference mirror; and
    determining, based on the one or more mirror measurements one or more calibration spectra.

14. The system of claim 13, wherein the one or more processors are further configured to perform operations comprising:
  performing, using the one or more mirror measurements, one or more of:
    calculating a dispersion-free k-spectrum;
    calculating a polynomial fit for the dispersion-free k-spectrum;
    calculating a dispersion spectrum; or
    calculating a spectral-flattening spectrum; and
  saving one or more of the calculated spectra and the polynomial fit as calibration spectra to memory.

15. The system of claim 14, wherein the one or more processors are further configured to perform operations comprising:
  loading the calibration spectra; and
  performing, using the loaded calibration spectra, one or more of: k-linearization, dispersion correction, or spectral flattening.

16. The system of claim 13,
  wherein the interferometer comprises a plurality of optical switches,
    at least two of the plurality of optical switches connected together by a length of optical fiber,
    when in a first position, the plurality of optical switches create a first optical path for optical signals to pass to and from the light source and the catheter, and
    when in a second position, the plurality of optical switches create a second optical path for optical signals to pass to and from a light source and the length of optical fiber; and
  one or more processors configured to perform operations comprising:
    receiving a back reflection of an optical signal at a connection point between the first and second optical connectors; and
    determining, based on the back reflection, whether the catheter is fully connected or not fully connected to the light source.

17. An imaging system comprising:
  a light source adapted to be coupled to a first optical connector;
  a catheter adapted to be coupled to a second optical connector, the first optical connector adapted to be coupled to the light source using the first optical connector and the second optical connector;
  an interferometer comprising one or more optical switches and a reference reflector coupled to a first optical switch of one or more optical switches; and
  one or more processors configured to perform operations comprising:
    receiving one or more mirror measurements using the reference reflector and a reference mirror;
    performing, using the one or more mirror measurements, one or more of:
      calculating a dispersion-free k-spectrum;
      calculating a polynomial fit for the dispersion-free k-spectrum;
      calculating a dispersion spectrum; or
      calculating a spectral-flattening spectrum; and
    saving one or more of the calculated spectra and the polynomial fit as calibration spectra to memory.

18. The system of claim 17, wherein the one or more processors are further configured to perform operations comprising:
  loading the calibration spectra; and
  performing, using the loaded calibration spectra, one or more of: k-linearization, dispersion correction, or spectral flattening.

19. The system of claim 18, wherein the one or more processors are configured to perform operations comprising:
  receiving an optical signal reflected by the reference reflector; and
  calculating system performance data, comprising one or more of a:
    point spread function,
    noise level,
    signal-to-noise ratio, or
    dynamic range.

20. The system of claim 17,
  wherein the sample arm comprises a plurality of optical switches,
    at least two of the plurality of optical switches connected together by a length of optical fiber,
    when in a first position, the plurality of optical switches create a first optical path for optical signals to pass to and from the light source and the catheter, and
    when in a second position, the plurality of optical switches create a second optical path for optical signals to pass to and from a light source and the length of optical fiber; and the one or more processors configured to perform operations comprising:
  receiving a back reflection of an optical signal at a connection point between the first and second optical connectors; and
  determining, based on the back reflection, whether the catheter is fully connected or not fully connected to the light source.

21. A method comprising operating an imaging system as in claim 1.

22. One or more non-transitory computer-readable storage media storing instructions that when executed by one or more processors, causes the one or more processors to perform operations as in claim 1.

* * * * *